United States Patent [19]

Pissiotas et al.

[11] Patent Number: 4,950,777
[45] Date of Patent: Aug. 21, 1990

[54] HERBICIDALLY ACTIVE DERIVATIVES OF N-PHENYL-3,4,5,6-TETRAHYDROPHTHALIMIDE

[75] Inventors: Georg Pissiotas, Lörrach, Fed. Rep. of Germany; Beat Böhner, Binningen, Switzerland

[73] Assignee: Ciba-Geigy Corporation, Ardsley, N.Y.

[21] Appl. No.: 303,431

[22] Filed: Jan. 30, 1989

Related U.S. Application Data

[62] Division of Ser. No. 874,765, Jun. 16, 1986, Pat. No. 4,824,476.

[30] Foreign Application Priority Data

Jun. 24, 1985 [CH] Switzerland .................. 2665/85
Jul. 25, 1985 [CH] Switzerland .................. 3237/85
Mar. 26, 1986 [CH] Switzerland .................. 1207/86

[51] Int. Cl.$^5$ .................. C07C 121/66; C07D 317/16
[52] U.S. Cl. .................. 558/301; 549/451
[58] Field of Search .................. 558/301; 549/451

[56] References Cited

U.S. PATENT DOCUMENTS

| | | | |
|---|---|---|---|
| 4,124,375 | 11/1978 | Ballinger et al. | 71/96 |
| 4,233,233 | 11/1980 | Schröer et al. | 260/465 |
| 4,260,555 | 4/1981 | Myatt | 71/105 X |
| 4,353,735 | 10/1982 | Fory et al. | 558/301 |
| 4,451,286 | 5/1984 | Martin | 71/118 |

FOREIGN PATENT DOCUMENTS 0003640  8/1979  European Pat. Off.
2831770  2/1979  Fed. Rep. of Germany.

OTHER PUBLICATIONS

Eicken et al., C.A.; 107:217479a (1987).
Chapman, Jr. et al.; J. of Med. Chem. (1983), 26, pp. 237–243.
Abstract of JP-A-59-128,371 (1984).
Chem. Abstract; 87:5357d; 87 (1977), Wagner et al.

*Primary Examiner*—Joseph Paul Brust
*Attorney, Agent, or Firm*—Kevin T. Mansfield

[57] ABSTRACT

Novel derivatives of N-phenyl-3,4,5,6-tetrahydrophthalimide of the formula I given below have good pre- and post-emergence, selective-herbicidal properties, and they furthermore regulate and inhibit plant growth. The compounds correspond to the formula I

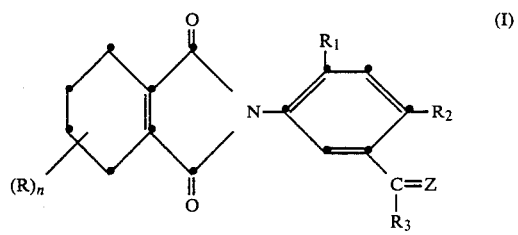

wherein
R is $C_1$–$C_3$-alkyl,
n is zero, one or two,
$R_1$ and $R_2$ independently of one another are each hydrogen or halogen,
$R_3$ is hydrogen, cyano, $C_1$–$C_4$-alkyl, $C_1$–$C_4$-haloalkyl or a radical —$CH_2YR_4$,
$R_4$ is $C_1$–$C_4$-alkyl, $C_3$–$C_4$-alkenyl, $C_3$–$C_4$-alkynyl, $C_3$–$C_7$-cycloalkyl, benzyl or phenyl,
Z is oxygen, or an oxime radical =N—O—Q, and the grouping —C($R_3$)=Z can also be a ketal radical, and
Q is hydrogen, a $C_1$–$C_{10}$-alkyl radical, a $C_3$–$C_8$-alkenyl radical or a $C_3$–$C_8$-alkynyl radical, a $C_3$–$C_7$-cycloalkyl or $C_3$–$C_7$-cycloalkenyl radical, a phenyl-$C_1$–$C_4$-alkyl group, a carbamoyl radical, a carbonic or thiocarbonic acid radical, a $C_1$–$C_4$-alkylsulfonyl radical, a metal ion or a quaternized ammonium ion.

3 Claims, No Drawings

HERBICIDALLY ACTIVE DERIVATIVES OF N-PHENYL-3,4,5,6-TETRAHYDROPHTHALIMIDE

This is a division of application Ser. No. 874,765, filed on June 16, 1986, now U.S. Pat. No 4,824,476, issued 4/25/89.

The present invention relates to novel derivatives of N-phenyl-3,4,5,6-tetrahydrophthalimide of the formula I having a herbicidal action and an action regulating plant growth, and also to the production of these novel compounds. The invention moreover relates to compositions containing the novel compounds, as well as to the application thereof for the selective control of weeds or for the regulation of plant growth.

The novel derivatives of N-phenyl-3,4,5,6-tetrahydrophthalimide correspond to the formula I

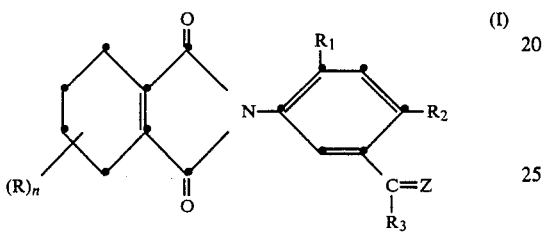

wherein
R is $C_1$-$C_3$-alkyl,
n is zero, one or two,
$R_1$ and $R_2$ independently of one another are each hydrogen or halogen,
$R_3$ is hydrogen, cyano, $C_1$-$C_4$-alkyl, $C_1$-$C_4$-haloalkyl or a radical —$CH_2YR_4$,
Y is oxygen or sulfur,
$R_4$ is $C_1$-$C_4$-alkyl, $C_3$-$C_4$-alkenyl, $C_3$-$C_4$-alkenyl, $C_3$-$C_7$-cycloalkyl, benzyl or phenyl, and the phenyl ring can be unsubstituted or substituted by $C_1$-$C_4$-alkyl, $C_1$-$C_4$-alkoxy, $C_1$-$C_4$-haloalkyl, $C_1$-$C_4$-haloalkoxy, nitro or cyano,
Z is oxygen or an oxime radical =N—O—Q, and the radical

can also be a ketal radical

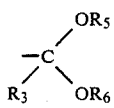

wherein
$R_5$ $R_6$ independently of one another are each $C_1$-$C_4$-alkyl, $C_1$-$C_4$-haloalkyl or $C_2$-$C_8$-alkoxyalkyl, or
$R_5$ and $R_6$ together are an ethylene bridge, a propylene bridge, or a cyclohexyl radical bound by way of adjacent carbon atoms, and the propylene bridge and the cyclohexyl radical can be substituted up to three times by $C_1$-$C_4$-alkyl groups, whilst the ethylene bridge can be mono- or disubstituted by $C_1$-$C_4$-alkyl, $C_1$-$C_4$-haloalkyl, $C_1$-$C_4$-hydroxyalkyl, $C_2$-$C_8$-alkoxyalkyl, $C_3$-$C_8$-alkoxyalkoxyalkyl, or by phenyl or benzyl unsubstituted or substituted by halogen or $C_1$-$C_4$-alkyl, or can be mono- or disubstituted by a radical —$CH_2YH$ or —$CH_2YR_4$, and Q is hydrogen, a $C_1$-$C_{10}$-alkyl radical which can be interrupted by oxygen, sulfur, —CO—, —CONH— or —NH—, or which can be substituted by halogen, cyano, hydroxyl, $C_1$-$C_6$-alkoxycarbonyl, $C_3$-$C_6$-alkenyloxycarbonyl, $C_3$-$C_6$-alkynyloxycarbonyl, $C_1$-$C_6$-alkylthiocarbonyl, $C_3$-$C_6$-alkenylthiocarbonyl, $C_3$-$C_6$-alkynylthiocarbonyl, carbamoyl or di-$C_1$-$C_4$-alkylcarbamoyl, or is a $C_3$-$C_8$-alkenyl or haloalkenyl radical, a $C_3$-$C_8$-alkynyl radical, a $C_3$-$C_7$-cycloalkyl or cycloalkenyl radical unsubstituted or substituted by halogen, or is a phenyl-$C_1$-$C_4$-alkyl radical, the phenyl nucleus of which can be substituted by halogen, $C_1$-$C_4$-alkyl, $C_1$-$C_4$-alkoxy, $C_1$-$C_4$-haloalkyl, $C_1$-$C_4$-haloalkoxy, nitro or cyano, or is a $C_1$-$C_{10}$-alkylcarbonyl, $C_3$-$C_{10}$-alkenylcarbonyl or $C_3$-$C_{10}$-alkynylcarbonyl radical, each of which can be interrupted by oxygen or substituted by halogen or cyano, or is a $C_1$-$C_{10}$-alkoxycarbonyl, $C_3$-$C_{10}$-alkenyloxycarbonyl or $C_3$-$C_{10}$-alkynyloxycarbonyl radical, each of which can be interrupted by oxygen or substituted by halogen or cyano, or is a $C_1$-$C_{10}$-alkoxythiocarbonyl, $C_3$-$C_{10}$-alkenylthiocarbonyl or $C_3$-$C_{10}$-alkynyloxythiocarbonyl radical, each of which can be interrupted by oxygen or substituted by halogen or cyano, or is an araliphatic, cycloaliphatic, aromatic or heterocyclic carbonyl or sulfonyl radical, each of which is unsubstituted in the ring or substituted by halogen, $C_1$-$C_4$-alkyl, $C_1$-$C_4$-alkoxy, $C_1$-$C_4$-haloalkoxy, nitro or cyano, or is a $C_1$-$C_4$-alkylsulfonyl radical, a sulfonamido or carbamoyl radical, each of which is unsubstituted or substituted by $C_1$-$C_4$-alkyl, or is a metal ion, a quaternised ammonium ion, or an araliphatic, cycloaliphatic or an unsubstituted or substituted aromatic or heterocyclic carbonic acid or thiocarbonic acid (bound by way of COO or CSO).

The present invention relates also to the stereoisomers and to the optically active enantiomers of these derivatives.

By halogen in the formula I is meant fluorine, chlorine, bromine or iodine, especially fluorine, chlorine or bromine.

The term 'alkyl' on its own or as part of another substituent embraces both branched-chain and straight-chain radicals. Examples are; methyl, ethyl, n-propyl, isopropyl, n-butyl, sec-butyl, tert-butyl and isobutyl, as well as the higher homologues: pentyl, hexyl, heptyl, octyl, and so forth, together with their isomers. In an analogous manner, alkanoyls and cyanoalkyls contain an additional carbon atom.

The alkenyl and alkynyl radicals can likewise be branched-chain or straight-chain, and include for example the groups: allyl, methallyl, butenyl, propanyl or butynyl and propynyl.

Preferred carboxylic acid esters and -thioesters are $C_1$-$C_4$-alkyl, $C_3$-$C_4$-alkenyl or $C_3$-$C_4$-alkynyl esters.

Carboxamides and sulfonamides denote, besides —$CONH_2$ and —$SO_2$—$NH_2$, respectively, also monoalkyl-substituted or symmetrically or unsymmetrically dialkyl-substituted or N-alkyl-N-alkoxy-substituted amides, the alkyl groups containing $C_1$-$C_4$ carbon atoms.

The term 'alkyl' on its own or as part of a substituent embraces both branched-chain and straight-chain $C_1$–$C_{10}$-alkyl groups; preferably, alone or as part of a substituent, they are $C_1$–$C_4$-alkyl groups. Examples are: methyl, ethyl, propyl, isopropyl, butyl, isobutyl, sec-butyl and tert-butyl, as well as the higher homologues: amyl, isoamyl, hexyl, heptyl, octyl, nonyl and decyl, together with their isomers. Analogously, alkanoyls or cyanoalkyls contain an additional C atom. Correspondingly, lower alkenyl or alkynyl groups contain a maximum of 4 C atoms The term 'aromatic group' embraces phenyl and naphthyl.

An araliphatic radical denotes an unsubstituted or mono- to trisubstituted phenyl or naphthyl group, which is linked by way of $C_1$–$C_4$-alkyl or $C_3$—$C_4$-alkenyl to the residue of the molecule. Examples are the basic substances benzyl, phenethyl and phenylallyl, as well as homologues thereof.

The term 'heterocyclic acyl radical' embraces 5- or 6-membered heterocyclic carboxyl compounds having a ring hetero atom from the group N, O or S. Examples are the radicals of furancarboxylic acid, thiophenecarboxylic acid, nicotinic, isonicotinic acid, and so forth.

A 5- to 10-membered heterocyclic radical Ar can be mono- or bicyclic.

Examples which may be mentioned from the group of monocyclic rings are: pyrrole, thiophene, furan, imidazole, pyrazole, oxazole, thiazole, thiadiazole, triazole, pyridine, pyrazine, pyrimidine, pyridazine and triazines, as well as partially or completely hydrogenated derivatives thereof, to which there also belong: azetidine, aziridine, morpholine, thiomorpholine, oxathiine, dioxane, dioxolane, dithiolane, dithiane, and the like.

From the bicyclic group of 5- to 10-membered heterocycles there may be mentioned the ring systems listed in the foregoing in combination with a fused-on benzene ring (for example benzofuran, indole, benzodioxolane, benzothiazole, benzoxazole, quinoline, benzothiodiazine, benzotriazine, and so forth), and also those with hetero atoms in both rings (for example quinolizidine, purine, and the like).

By the incorporation of an oxo and/or thiono group, further heterocyclic ring systems are formed, for example: hydantoin, thiohydantoin, triazinone, coumarin, pyridinone, maleic hydrazide, maleic anhydride, glutaric anhydride, barbituric acid, and so forth. N-Heterocycles embrace also N oxides.

Cycloalkyl groups are: cyclopropyl, cyclobutyl, cyclopentyl, cyclohexyl and cycloheptyl. Cycloaliphatic radicals correspond to these ring systems, but they can contain in addition, depending on the possibility, one or more double bonds.

By metal ions are meant in this case cations of the I to IV groups of the periodic system, and also heavy metal salts. Examples are: Na, K, Ca, Mg, Al, Zn, Cu, Fe, Mn, Co and Ni.

Quaternary ammonium ions contain, as identical or different substituents: hydrogen, $C_1$–$C_{12}$-alkyl, lower hydroxyalkyl, benzyl, amino or di-$C_1$–$C_4$-alkylamino, or they form from two valencies and the N atom a 5- or 6-membered heterocyclic ring optionally having a further hetero atom N, O or S.

The novel derivatives of the N-phenyl-3,4,5,6-tetrahydrophthalimide of the formula I are characterised by a herbicidal action, and can be used for controlling weeds. Depending on the dosage, they act as total or selective herbicides, and can be used for the control of weeds in crops of cultivated plants.

These compounds likewise have an action regulating plant growth, and can be used to inhibit plant growth.

Compounds which have proved particularly active are the keto compounds corresponding to the formula Ia

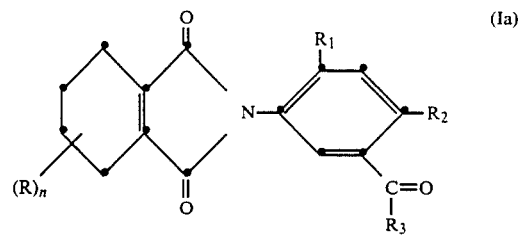

wherein $R_3$ is hydrogen, $C_1$–$C_4$-alkyl or a radical —$CH_2YR_4$, and n, R, $R_1$, $R_2$ and $R_4$ have the meanings defined under the formula I, in particular:

2-chloro-4-fluoro-5-(N-3,4,5,6-tetrahydrophthalimido)acetophenone, 4-fluoro-5-(N-3,4,5,6-tetrahydrophthalimido)-acetophenone, and 2-bromo-4-fluoro-5-(N-3,4,5,6-tetrahydrophthalimido)acetophenone.

Likewise very active are the ketal compounds of the formula Ib

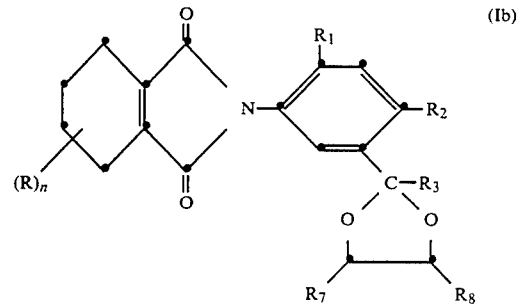

wherein $R_3$, $R_7$ and $R_8$ independently of one another are each hydrogen or $C_1$–$C_4$-alkyl, and n, R, $R_1$ and $R_2$ have the meanings defined under the formula I, in particular the compounds:

N-[2-fluoro-4-chloro-5-(2-methyl-1,3-dioxalon-2-yl)-phenyl]-3,4,5,6-tetrahydrophthalimide, N-[2-fluoro-4-chloro-5-(2,4-dimethyl-1,3-dioxolan-2-yl)phenyl]-3,4,5,6-tetrahydrophthalimide, N-[2-fluoro-4-chloro-5-(4-ethyl-2-methyl-1,3-dioxolan-2-yl)-phenyl]-3,4,5,6-tetrahydrophthalimide, N-2-fluoro-5-(2-methyl-1,3-dioxolan-2-yl)-phenyl]-3,4,5,6-tetrahydrophthalimide, N-[2,4-difluoro-5-(2,4-dimethyl-1,3-dioxolan-2-yl)-phenyl]-3,4,5,6-tetrahydrophthalimide, N-[2,4-difluoro-5-(2,4,5-trimethyl-1,3-dioxolan-2-yl)-phenyl]-3,4,5,6-tetrahydrophthalimide, N-[4-fluoro-5-(4-ethyl-2-methyl-1,3-dioxolan-2-yl)-phenyl]-3,4,5,6-tetrahydrophthalimide, and N-[2-fluoro-4-chloro-5-(2,4,5-trimethyl-1,3-dioxolan-2-yl)-phenyl]-3,4,5,6-tetrahydrophthalimide.

A very good action is exhibited also by the oxime compounds of the formula Ic

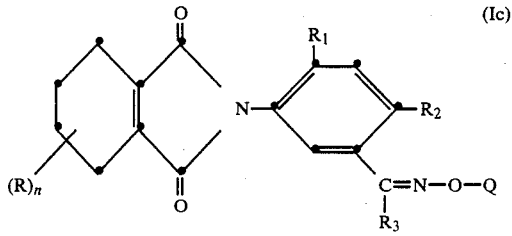

wherein
n, $R_1$ and R have the meanings defined under the formula I,
$R_3$ is methyl or cyano, and
Q is hydrogen, a $C_1$–$C_{10}$-alkyl group which can be interrupted by oxygen, sulfur, —CO—, —CONH or NH—, or can be substituted by halogen, cyano, hydroxyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_3$–$C_6$-alkenylthiocarbonyl, $C_3$–$C_6$-alkynylthiocarbonyl, carbamoyl or di-$C_1$–$C_4$-alkylcarbamoyl, or is a $C_3$–$C_8$-alkenyl or haloalkenyl radical, a $C_3$–$C_8$-alkynyl radical, a phenyl-$C_1$–$C_4$-alkyl radical of which the phenyl nucleus can be substituted by halogen, $C_1$–$C_4$-alkyl, $C_1$–$C_4$-alkoxy, $C_1$–$C_4$-haloalkyl, $C_1$–$C_4$-haloalkoxy, nitro or cyano, or is a $C_1$–$C_4$-alkylcarbonyl radical, a $C_1$–$C_4$-alkylthiocarbonyl radical, a $C_1$–$C_4$-alkylsulfonyl radical or a $C_1$–$C_4$-alkylcarbamoyl radical or $C_1$–$C_4$-alkylthiocarbamoyl radical, especially the compounds:
2-chloro-4-fluoro-5-(N-3,4,5,6-tetrahydrophthalimido)-acetophenone oxime,
4-fluoro-5-(N-3,4,5,6-tetrahydrophthalimido)-acetophenone oxime,
2-chloro-4-fluoro-5-(N-3,4,5,6-tetrahydrophthalimido)-acetophenoneoxime-(methoxycarbonyleth-1-yl) ether,
4-fluoro-5-(N-3,4,5,6-tetrahydrophthalimido)-acetophenoneoxime-(methoxycarbonyleth-1-yl) ether,
2,4-dichloro-5-(N-3,4,5,6-tetrahydrophthalimido)-acetophenoneoxime-(methoxycarbonyleth-1-yl) ether,
2-chloro-4-fluoro-5-(N-3,4,5,6-tetrahydrophthalimido)-acetophenoneoxime-methyl ether,
2-chloro-4-fluoro-5-(N-3,4,5,6-tetrahydrophthalimido)-acetophenoneoxime-ethyl ether,
2-chloro-4-fluoro-5-(N-3,4,5,6-tetrahydrophthalimido)-acetophenoneoxime-n-butyl ether,
2-chloro-4-fluoro-5-(N-3,4,5,6-tetrahydrophthalimido)-acetophenoneoxime-t-butyl ether,
2-chloro-4-fluoro-5-(N-3,4,5,6-tetrahydrophthalimido)-acetophenoneoxime-benzyl ether,
2-chloro-4-fluoro-5-(N-3,4,5,6-tetrahydrophthalimido)-acetophenoneoxime-(2-chlorobenzyl) ether, and
2,4-difluoro-5-(N-3,4,5,6-tetrahydrophthalimido)-acetophenoneoxime-(2-chlorobenzyl) ether.

Finally, a good action is exhibited also by those compounds of the formula Ic wherein n is zero, $R_3$ is cyano, and Q is hydrogen or $C_1$–$C_{10}$-alkyl unsubstituted or substituted by halogen or $C_1$–$C_6$-alkoxycarbonyl, or is $C_3$–$C_8$-alkenyl or haloalkenyl, benzyl or halobenzyl, whilst $R_1$ and $R_2$ have the meanings defined under the formula I, particularly by the compounds:
methoximino-[2-chloro-4-fluoro-5-(N-3,4,5,6-tetrahydrophthalimido)-benzoyl cyanides,
ethoximino-[2-chloro-4-fluoro-5-(N-3,4,5,6-tetrahydrophthalimido)]-benzoyl cyanides,
isopropoximino-[2-chloro-4-fluoro-5-(N-3,4,5,6-tetrahydrophthalimido)]-benzoyl cyanides,
sec-butoximino-[2-chloro-4-fluoro-5-(N-3,4,5,6-tetrahydrophthalimido)]-benzoyl cyanides, and
methoxycarbonyl-eth-1-oximino-2-chloro-4-fluoro-5-(N-3,4,5,6-tetrahydrophthalimido)-benzoyl cyanides.

The N-phenyl-3,4,5,6-tetrahydrophthalimides of the formula I according to the invention are produced by methods known per se.

The process according to the invention for producing the derivatives of N-phenyl-3,4,5,6-tetrahydrophthalimide of the formula I comprises reacting the anhydride of a 3,4,5,6-tetrahydrophthalic acid of the formula II

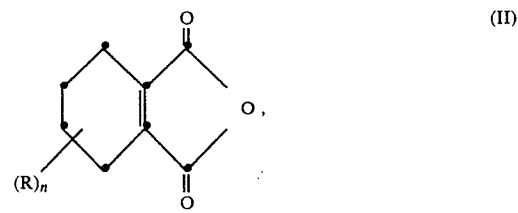

wherein n and R have the meanings defined under the formula I, in an inert organic solvent or diluent, optionally in the presence of a small amount of a dehydrating agent, with the equimolar amount of a 3-aminophenone or oxime of the formula V

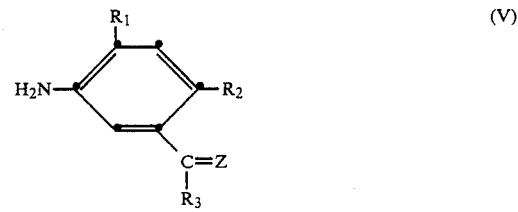

wherein $R_1$, $R_2$, $R_3$ and Z have the meanings defined under the formula I.

The novel keto and ketal derivatives of the N-phenyl-3,4,5,6-tetrahydrophthalimide of the formula Ia are produced according to the invention by reacting the anhydride of a 3,4,5,6-tetrahydrophthalic acid of the formula II

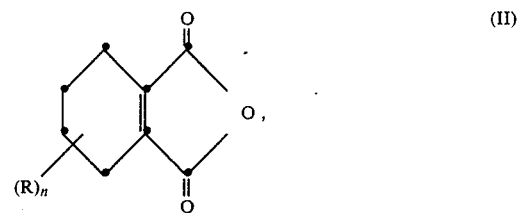

wherein R and n have the meanings defined under the formula I, in an inert organic solvent or diluent, optionally in the presence of a small amount of a dehydrating agent, with the equimolar amount of a 3-aminophenone of the formula III

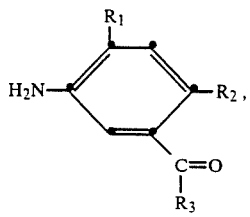

wherein $R_1$, $R_2$ and $R_3$ have the meanings defined under the formula I; and, in the case where Z has a meaning other than oxygen, reacting this product, in an inert solvent in the presence of an acid, with an alcohol or a diol of the formulae IV and IVa, respectively,

HO—$R_5$ (IV)

HO—$R_5$—$R_6$—OH (IVa), wherein $R_5$ and $R_6$ have the meanings defined under the formula I.

Suitable solvents or diluents for this reaction are high-boiling hydrocarbons, low alkanoic acids as well as esters thereof, and high-boiling ketones and ethers. Mentioned as examples are: toluene, xylene, acetic acid, ethyl acetate, isopropyl ether, tetrahydrofuran, methyl ethyl ketone and dimethylformamide.

The reaction is performed at a temperature lying between room temperature and the boiling point of the reaction mixture.

In order to accelerate the reaction, there can be added a small amount of a dehydrating or water-absorbing agent, for example sulfuric acid or an organic sulfonic acid, or of a salt, such as sodium acetate, or of an anhydride, such as phosphorus pentoxide.

The 3-aminophenone of the formula III can be produced for example according to the following synthesis:

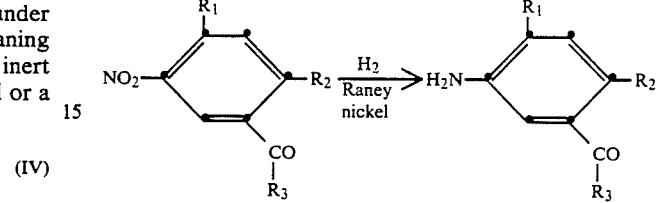

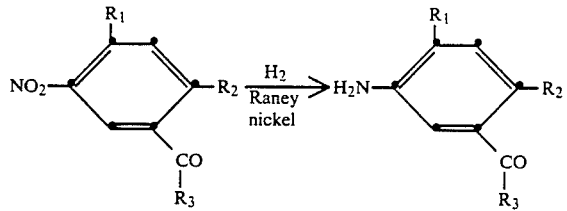

A phenone correspondingly substituted in the phenyl nucleus is nitrated with a nitric acid mixture, and the formed 3-nitrophenone is subsequently reduced with hydrogen, for example in the presence of Raney nickel, to 3-aminophenone. The amine is then subjected to a condensation reaction with a 3,4,5,6-tetrahydrophthalic anhydride, according to the process of the invention.

5-(N-3,4,5,6-Tetraphthalimido)-phenone derivatives of the formula I in which $R_3$ is a radical —$CH_2$—$YR_4$, and Z together with the carbon atom forms a radical

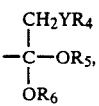

wherein n, R, $R_1$, $R_2$, $R_4$, $R_5$, $R_6$ and Y have the meanings defined under the formula I, can be produced for example by the reactions shown in the following diagram:

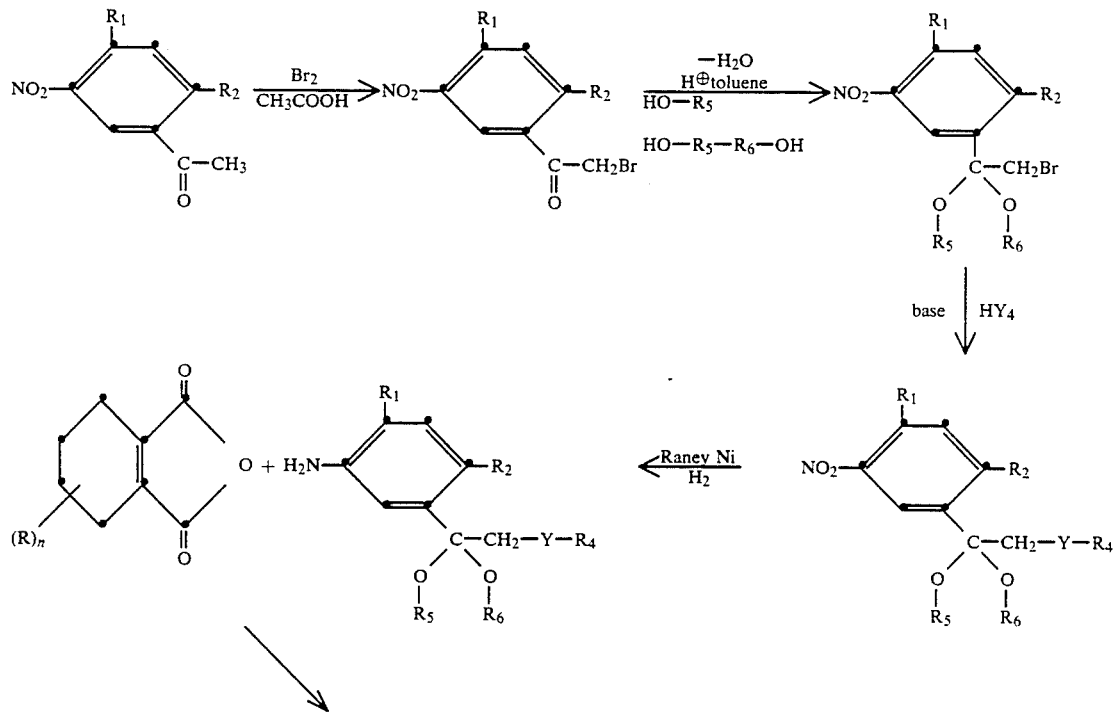

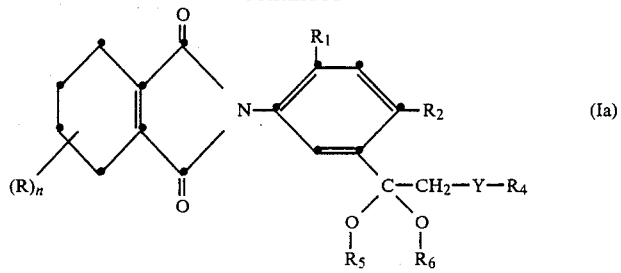

(Ia)

A 3-nitroacetophenone substituted by $R_1$ and $R_2$ is brominated in acetic acid to obtain α-bromo-3-nitroacetophenone, which is subsequently reacted in an inert solvent, in the presence of an acid, with alcohol or a diol of the formula IV to the α-bromo-3-nitroacetophenone ketal. This ketal is then reduced with a reducing agent, for example hydrogen in the presence of Raney nickel or tin and dilute hydrochloric acid or lithium aluminium hydride, to the 3-aminoacetophenone ketal, which is afterwards reacted according to the invention with the anhydride of a 3,4,5,6-tetrahydrophthalic acid of the formula II.

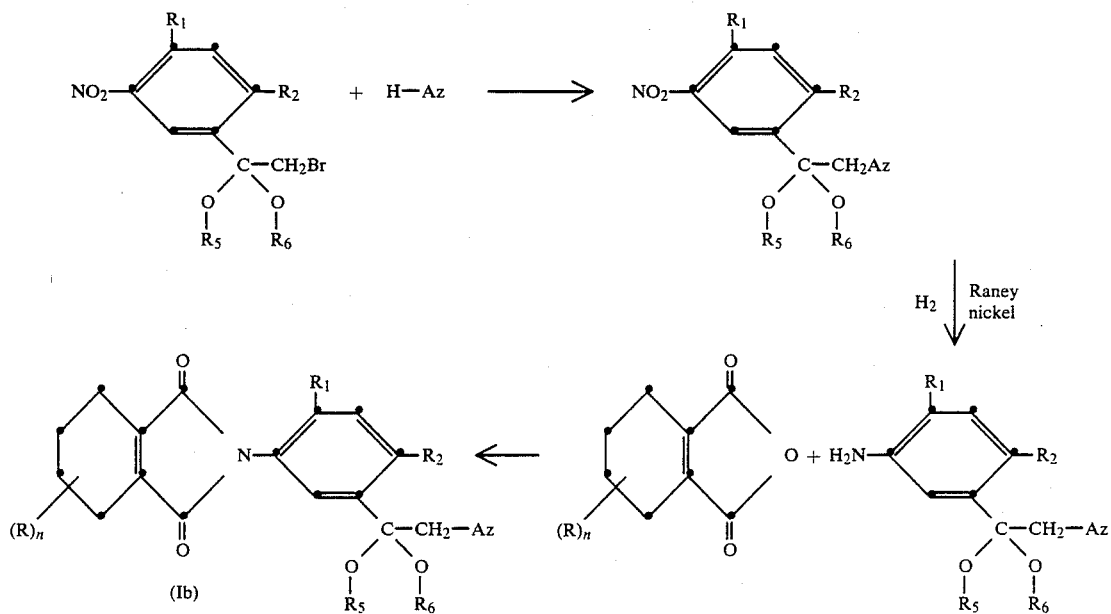

(Ib)

In these formulae, Az is the imidazol-1-yl, 1,2,4-triazol-1-yl or 1,3,4-triazol-1-yl radical, and n, R, $R_1$, $R_2$, $R_5$ and $R_6$ have the meanings defined under the formula I.

An α-bromo-3-nitroacetophenone ketal correspondingly substituted by $R_1$, $R_2$, $R_5$ and $R_6$ is subjected to a condensation reaction with imidazole or 1,2,4- or 1,3,4-triazole to obtain the α-azolyl-3-nitroacetophenone ketal. This product is then reduced, for example with hydrogen and Raney nickel or tin and dilute hydrochloric acid or lithium aluminium or boron hydride, whereupon there is formed the corresponding α-azolyl-3-aminoacetophenone ketal, which is reacted according to the invention with the anhydride of a 3,4,5,6-tetrahydrophthalic acid of the formula II.

The novel oxime derivatives of the N-phenyl-3,4,5,6-tetrahydrophthalimide of the formula Ic are produced according to the invention by reacting a salt of the formula VII

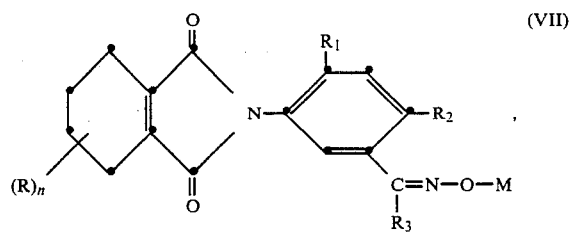

(VII)

in which M is an alkali metal cation or alkaline-earth metal cation, and n, R, $R_1$, $R_2$ and $R_3$ have the meanings defined in the foregoing, with a reactive ester of the formula VIII

Y—Q (VIII)

wherein Q has the meaning defined under the formula I, and Y is an organic or inorganic acid radical.

Suitable salts of an oxime of the formula VII are in particular the sodium and potassium salts. The reaction of the oxime of the formula VII with the reactive ester of the formula VIII is advantageously performed in an inert organic solvent. Especially suitable are polar solvents, such as acetonitrile, dimethylformamide, acetone, dimethylacetamide, methylpyrrolidone and dimethyl sulfoxide. The reactants are used as a rule in equimolar amounts. The one or other reactant can however be used in excess in order to effect the complete course of reaction. Suitable reactive acid esters are particularly the halides but also sulfonic acid radicals, for example of methyl-, ethyl-, phenyl- or toluenesulfonic acid. The reaction is carried out advantageously at a temperature of 60°-90° C. When another solvent is employed, for example toluene or chlorobenzene, the reaction is performed at a higher temperature and with a longer reaction time.

According to the U.S. Pat. No. 4,260,555, the radical Q is esterified with a sulfonic acid radical, and the resulting ester of the formula IX

Z—SO₃—Q        (IX), wherein Z is a lower alkyl group or a phenyl group substituted by lower alkyl or halogen, is reacted with the oxime of the formula VII or with a salt thereof The oximes of the formula Ic can be produced in a known manner by reaction of the corresponding ketones with hydroxylamine. The ketones required for this purpose can for their part be obtained by the reaction sequences shown in the following diagram:

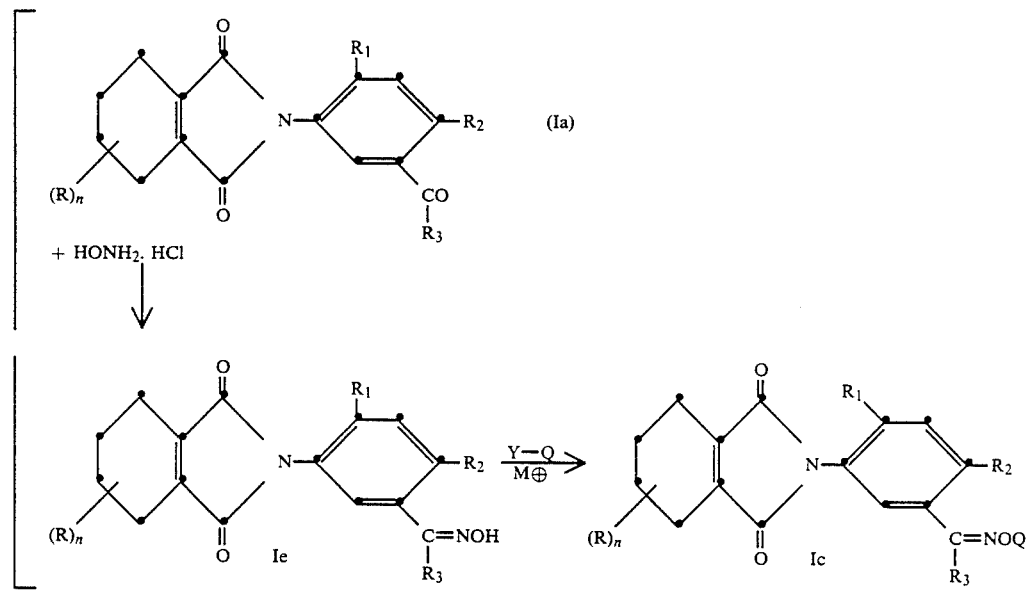

A 3-(N-3,4,5,6-tetrahydrophthalimido)-phenone correspondingly substituted in the phenyl nucleus is treated with hydroxylamine hydrochloride, in the course of which there is formed an oxime derivative of N-phenyl-3,4,5,6-tetrahydrophthalimide according to the formula Ie, in which Q is hydrogen. If it is desired to produce other derivatives of these compounds in which Q has a meaning other than hydrogen, the above oxime is firstly treated with an alkali metal base or alkaline-earth metal base, and subsequently with a reactive ester A-Q, wherein A is for example a halide or an alkyl- or tolylsulfonyl acid radical.

A further sequence of reactions for producing 5-(N-3,4,5,6-tetrahydrophthalimino)-acetophenoximes of the formula Ic ca be illustrated by the following diagram:

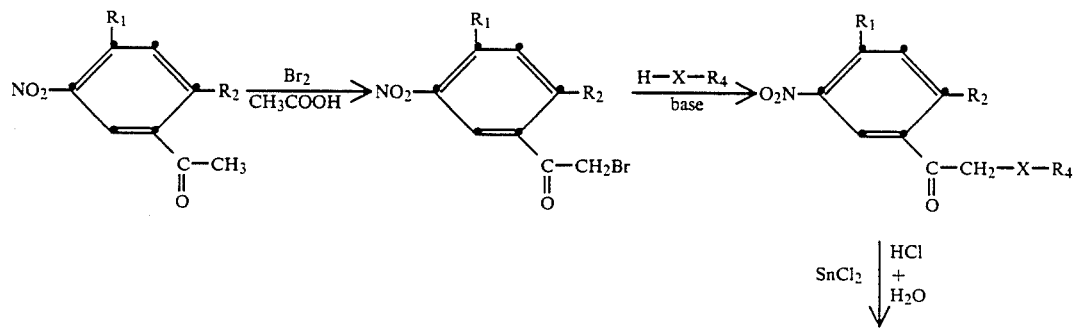

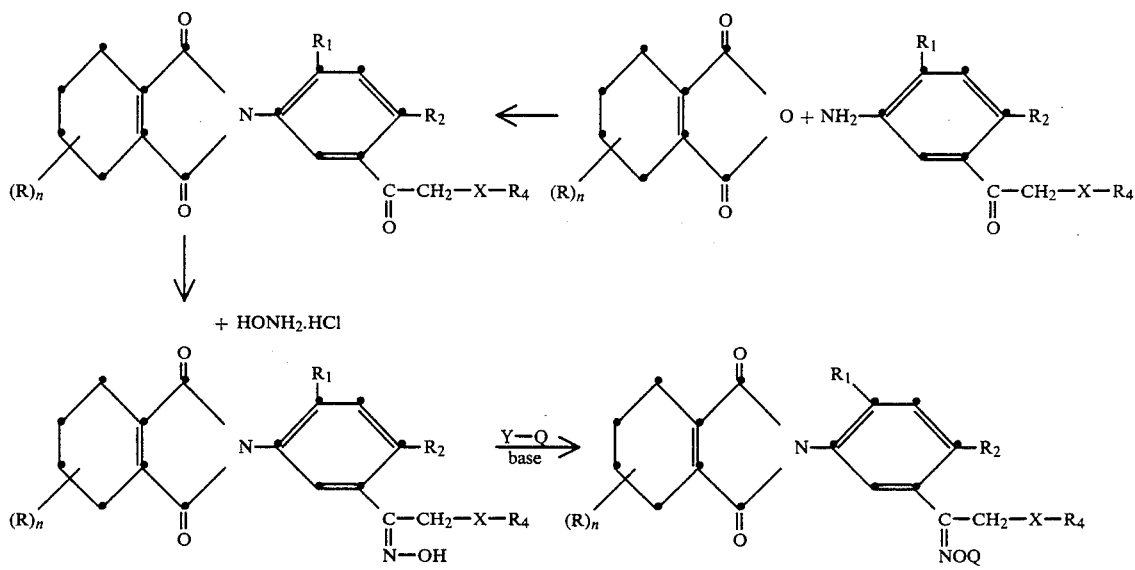

A 3-nitroacetophenone is converted by bromination in acetic acid into α-bromo-3-nitroacetophenone, and this is then etherified with an alcohol or thiol compound in the presence of a base. The nitro group is subsequently reduced with tin chloride, in the presence of hydrochloric acid and water, to the amino group. The 5-aminoacetophenone ether or -thio ether is now subjected to a condensation reaction with the anhydride of an unsubstituted or alkyl-substituted 3,4,5,6-tetrahydrophthalic anhydride. The 5-(N-3,4,5,6-tetrahydrophthalimido)-acetophenone thus obtained is further converted with hydroxylamine hydrochloride into the acetophenoxime, and, if an oxime ether is desired, the oxime is converted with an alkali metal base or alkaline-earth metal base into the salt, and this is subsequently converted with a reactive ester Y-Q into an oxime ether of the formula I.

Finally, the novel oxime derivatives of the formula I can be produced also by a further reaction sequence shown in the following diagram;

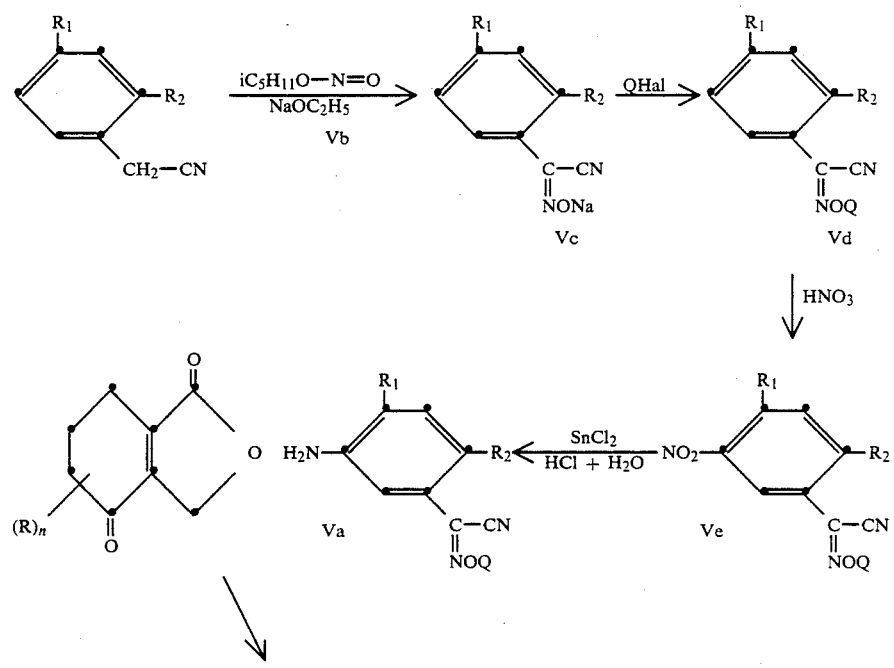

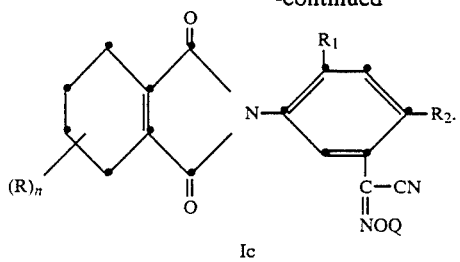

Ic

A cyanobenzyl of the formula Vb substituted in the 5- and 4-position by $R_1$ and $R_2$ is treated, in the presence of sodium ethylate, with isopentyl nitrite, in the process of which is formed the cyanoacetoxime sodium salt of the formula Vc, which is etherified with a halide of the formula QX-Hal. The cyanoacetoxime ether of the formula Vd obtained is nitrated with nitric acid, and the nitro group is reduced with tin chloride in aqueous hydrochloric acid. There is thus obtained a 3-aminophenylcyanoacetoxime ether, which is subjected to a condensation reaction with 3,4,5,6-tetrahydrophthalic anhydride to obtain the compound of the formula I.

In the above formulae, n, R, $R_1$, $R_2$ and Q have the meanings defined under the formula I, and X is a halogen atom.

A further process for producing the oxime derivatives of N-phenyl-3,4,5,6-tetrahydrophthalimide of the formula Ic comprises reacting an anhydride of a 3,4,5,6-tetrahydrophthalic acid of the formula II, in an inert organic solvent or diluent, optionally in the presence of a base with a 3-aminophenoxime ether of the above formula Va.

The 3-aminophenoxime ethers of the formula Va are produced also by starting with benzyl cyanides corresponding to the following reaction pattern:

to obtain 3-aminophenoxime ether of the formula Va. This can be subjected to a condensation reaction, as described above, with the 3,4,5,6-tetrahydrophthalic anhydride of the formula II.

The 3-aminophenoxime ethers of the formula Va are novel products. They and the production thereof likewise form subject matter of the present invention.

The active substances of the formula I are as a rule successfully applied in amounts of 0.005 to 4 kg per hectare, especially 0.001 to 1 kg per hectare.

In lower applied amounts, the compounds of the formula I are distinguished by good selective growth-inhibiting and selective herbicidal properties, which render them excellently suitable for use in crops of cultivated plants, especially in crops of cereals, cotton, soya bean, maize and rice. It is also possible in some cases to destroy weeds which could be dealt with hitherto only by the application of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at their roots. The novel compounds of the formula I are effective in ap-

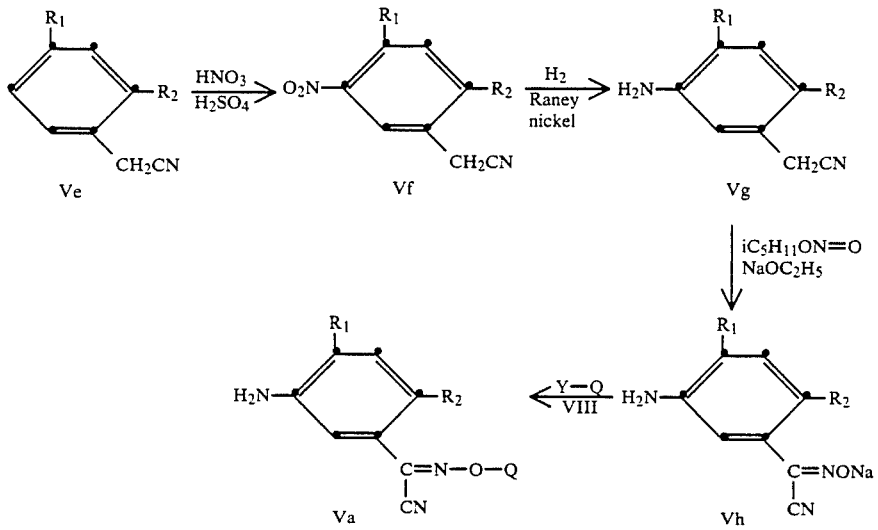

A correspondingly substituted benzyl cyanide of the formula Ve is nitrated in concentrated sulfuric acid. The formed 3-nitrobenzyl cyanide of the formula Vf is subsequently hydrogenated in the presence of a catalyst with hydrogen to obtain 3-aminobenzyl cyanide of the formula Vg. By treatment with isopentyl nitrite in the presence of sodium and ethanol, there is formed the Na salt of 3-aminobenzoyl cyanide oxime of the formula Vh, which is reacted with an ester of the formula VIII plied amounts which are very small compared with the amounts required to obtain the same effect using other herbicides and plant-growth regulators.

The compounds of the formula I also have excellent properties for inhibiting plant growth. Both monocotyledons and dicotyledon are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

A reduction of the vegetative growth enables in the case of many cultivated plants the crop density to be increased, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

With larger applied amounts of active substance, all the tested plants are impaired in their development to the extent that they wither.

The present invention relates also to herbicidal and plant-growth-regulating compositions containing a novel active ingredient of the formula I, and also to processes for the pre- and post-emergence controlling of weeds, and for the reduction of growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soyabean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salts of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4-14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanol, castor oil polyglycol ethers, polypropylene/polyethyleneoxy adducts, tributylphenoxypolyethoxyethanol, polyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1979; and Dr. Helmut Stache, "Tenside Taschenbuch", Carl Hanser Verlag, Munich/Vienna, 1981.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25%, of a tenside.

Preferred formulations are made up in particular as follows (%=per cent by weight):

| Emulsifiable concentrates | | |
|---|---|---|
| active ingredient of the formula I: | 1 to 20%, preferably | 5 to 10% |
| surface-active agent: | 5 to 30%, preferably | 10 to 20% |
| liquid carrier: | 50 to 94%, preferably | 70 to 85%. |
| Dusts | | |
| active ingredient of the formula I: | 0.1 to 10%, preferably | 0.1 to 1% |
| solid carrier: | 99.9 to 90%, preferably | 99.9 to 99%. |
| Suspension concentrates | | |
| active ingredient of the formula I: | 5 to 75%, preferably | 10 to 50% |
| water: | 94 to 25%, preferably | 90 to 30% |
| surface-active agent: | 1 to 40%, preferably | 2 to 30%. |
| Wettable powders | | |
| active ingredient of the formula I: | 0.5 to 90%, preferably | 1 to 80% |
| surface-active agent: | 0.5 to 20%, preferably | 1 to 15% |
| solid carrier: | 5 to 95%, preferably | 15 to 90%. |
| Granulates | | |
| active ingredient of the formula I: | 0.5 to 30%, preferably | 3 to 15% |
| solid carrier: | 99.5 to 70%, preferably | 97 to 85%. |

Whereas commercial products are preferably in the form of concentrated compositions, the compositions employed by the end-user are as a rule diluted. The preparations can on application be diluted down to 0.001% of active ingredient. The applied amounts are usually 0.005 to 5 kg of active substance per hectare.

The compositions can also contain further additives, such as stabilisers, antifoaming agents, viscosity regulators, binders and adhesives, as well as fertilisers or other active substances for obtaining special effects.

The following Examples illustrate the production of some derivatives of N-phenyl-3,4,5,6-tetrahydrophthalimide of the formula I according to the invention. Further compounds produced in a corresponding manner are listed in the subsequently given Tables. Temperatures are given in degrees Centigrade and pressure values are in millibars.

EXAMPLE 1

Production of 2-chloro-4-fluoro-5-(N-3,4,5,6-tetrahydrophthalimido)-acetophenone

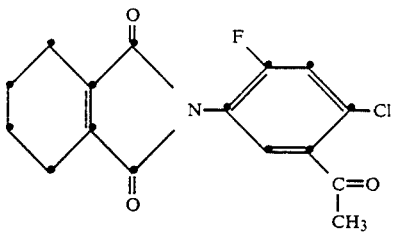

A mixture of 18.8 g of 2-chloro-4-fluoro-5-aminoacetophenone, 15.2 g of 3,4,5,6-tetrahydrophthalic anhydride and 300 ml of glacial acetic acid is refluxed with stirring for 8 hours. The reaction mixture is then poured onto ice, and the product which precipitates is extracted with ethyl acetate. The organic phase is dried over sodium sulfate and subsequently concentrated in vacuo. The residue is recrystallised in methanol to thus obtain 26.1 g of 2-chloro-4-fluoro-5-(N-3,4,5,6-tetrahydrophthalimido)-acetophenone having a melting point of 114° C.

The 2-chloro-4-fluoro-5-aminoacetophenone required as starting material is produced as follows:

(a) 2-Chloro-4-fluoro-5-nitroacetophenone

To 500 ml of fuming nitric acid are added dropwise with stirring, at a temperature of 0° C., 88 g of 2-chloro-4fluoroacetophenone. After being stirred for two hours at this temperature, the reaction mixture is poured onto ice; the product which has precipitated is filtered off with suction, and washed with cold ether. The yield is 63 g of 2-chloro-4-fluoro-5-nitroacetophenone having a melting point of 64°-65° C.

(b) 2-Chloro-4-fluoro-5-aminoacetophenone

Hydrogen is introduced at 20°-25° C. under normal pressure into a mixture of 97 g of 2-chloro-4-fluoro-5-nitroacetophenone, 20 g of Raney nickel and 1 liter of tetrahydrofuran until the stoichiometric amount of hydrogen has been absorbed. After completion of the reaction, filtration is performed, and the filtrate is concentrated in vacuo. The residue is crystallised from toluene/cyclohexane to thus obtain 70 g of 2-chloro-4-fluoro-5aminoacetophenone having a melting point of 95°-96° C.

In a manner analogous to that of this Example are produced the 5-(N-3,4,5,6-tetrahydrophthalimido)-acetophenone derivatives listed in Table 1.

TABLE 1

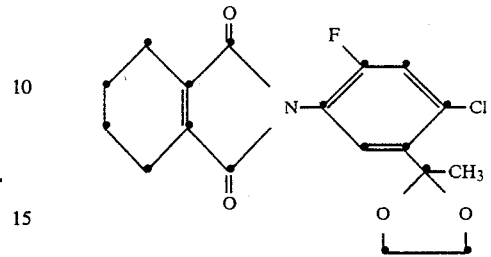

| No. | (R)$_n$ | R$_1$ | R$_2$ | R$_3$ | Physical data (°C.) |
|---|---|---|---|---|---|
| 1.01 | — | F | Cl | CH$_3$ | m.p. 114° |
| 1.02 | — | F | H | CH$_3$ | m.p. 123–124° |
| 1.03 | — | F | F | CH$_3$ | m.p. 124–125° |
| 1.04 | — | Cl | Cl | CH$_3$ | m.p. 130–131° |
| 1.05 | — | F | Cl | CH(CH$_3$)$_2$ | |
| 1.06 | — | F | Cl | CH(CH$_3$)$_2$ | |
| 1.07 | — | F | F | CH(CH$_3$)$_2$ | |
| 1.08 | — | Cl | Cl | CH(CH$_3$)$_2$ | |
| 1.09 | 4-CH$_3$ | F | Cl | CH$_3$ | |
| 1.10 | 4-CH$_3$ | F | H | CH$_3$ | |
| 1.11 | 4-CH$_3$ | F | F | CH$_3$ | |
| 1.12 | 4-CH$_3$ | Cl | Cl | CH$_3$ | |
| 1.13 | — | F | Cl | CF$_3$ | |
| 1.14 | — | F | H | CF$_3$ | |
| 1.15 | — | F | F | CF$_3$ | |
| 1.16 | — | Cl | Cl | CF$_3$ | |
| 1.17 | — | F | Cl | CH$_2$OCH$_2$—CH=CH$_2$ | |
| 1.18 | — | F | H | CH$_2$OCH$_2$—CH=CH$_2$ | |
| 1.19 | — | F | F | CH$_2$OCH$_2$—CH=CH$_2$ | |
| 1.20 | — | Cl | Cl | CH$_2$OCH$_2$—CH=CH$_2$ | |
| 1.21 | 4-CH$_3$ | F | Cl | CH$_2$O-benzyl | |
| 1.22 | 4-CH$_3$ | F | H | CH$_2$O-benzyl | |
| 1.23 | 4-CH$_3$ | F | F | CH$_2$O-benzyl | |
| 1.24 | 4-CH$_3$ | Cl | Cl | CH$_2$O-benzyl | |
| 1.25 | — | F | Cl | CH$_2$OCH(CH$_3$)$_2$ | |
| 1.26 | — | F | H | CH$_2$OCH(CH$_3$)$_2$ | |
| 1.27 | — | F | F | CH$_2$OCH$_2$(CH$_3$)$_2$ | |
| 1.28 | — | Cl | Cl | CH$_2$OCH$_2$(CH$_3$)$_2$ | |
| 1.29 | — | F | Br | CH$_3$ | m.p. 124–5° |
| 1.30 | — | F | Cl | CH$_2$—Br | m.p. 82° |
| 1.31 | 4-CH$_3$ | F | Br | CH$_3$ | |
| 1.32 | 3-CH$_3$ | F | Br | CH$_3$ | |

EXAMPLE 2

Production of N-[2-fluoro-4-chloro-5-(2-methyl-1,3-dioxolan-2-yl)-phenyl]-3,4,5,6-tetrahydrophthalimide

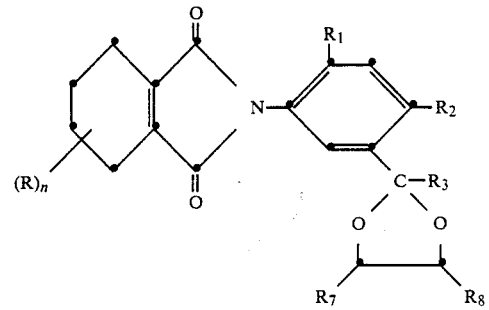

A mixture of 4.6 g of 2-chloro-4-fluoro-5-(N-3,4,5,6-tetrahydrophthalimido)-acetophenone, 1 g of ethylene glycol, 0.2 g of p-toluenesulfonic acid and 100 ml of benzene is boiled for 12 hours on a water separator. The reaction mixture is then filtered and the solution concentrated by evaporation. The residue is recrystallised from hexane to thus obtain 3.8 g of the title product having a melting point of 147° C.

In a manner analogous to that described in this Example, there are obtained the acetal derivatives of 5-(N-3,4,5,6-tetrahydropthalimido)-phenone which are listed in Table 2.

TABLE 2

| No. | (R)$_n$ | R$_1$ | R$_2$ | R$_3$ | R$_7$ | R$_8$ | Physical data (°C.) |
|---|---|---|---|---|---|---|---|
| 2.01 | — | F | Cl | CH$_3$ | H | H | m.p. 147° |
| 2.02 | — | F | Cl | CH$_3$ | CH$_3$ | H | m.p. 78° C. |
| 2.03 | — | F | Cl | CH$_3$ | C$_2$H$_5$ | H | $n_D^{30}$ 1.5227 |
| 2.04 | — | F | Cl | CH$_3$ | C$_3$H$_7$n | H | |
| 2.05 | 3-CH$_3$ | F | Cl | CH$_3$ | CH(CH$_3$)$_2$ | H | |
| 2.06 | — | F | Cl | CH$_3$ | C$_4$H$_9$n | H | |
| 2.07 | 3,4-(CH$_3$)$_2$ | F | Cl | CH$_3$ | CH$_2$CH(CH$_3$)$_2$ | H | |
| 2.08 | — | F | Cl | CH$_3$ | CH$_2$Cl | H | $n_D^{26}$ 1.5401 |
| 2.09 | — | F | Cl | CH$_3$ | CH$_2$OH | H | $n_D^{26}$ 1.5513 |
| 2.10 | — | F | Cl | CH$_3$ | CH$_2$O-(4-chlorobenzyl) | H | |
| 2.11 | — | F | Cl | CH$_3$ | CH$_2$O-(4-methylbenzyl) | H | |
| 2.12 | — | F | Cl | CH$_3$ | CH$_2$OCH$_3$ | H | |
| 2.13 | — | F | Cl | CH$_3$ | CH$_2$OC$_2$H$_5$ | H | |
| 2.14 | — | F | Cl | CH$_3$ | CH$_2$OC$_2$H$_4$OCH$_3$ | H | |

TABLE 2-continued

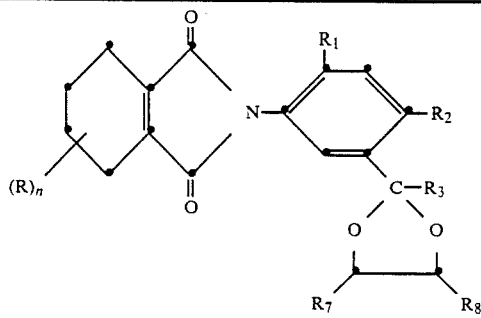

| No. | (R)$_n$ | R$_1$ | R$_2$ | R$_3$ | R$_7$ | R$_8$ | Physical data (°C.) |
|---|---|---|---|---|---|---|---|
| 2.15 | — | F | Cl | CH$_3$ | CH$_2$OCH$_2$CH=CH$_2$ | H | |
| 2.16 | — | F | Cl | CH$_3$ | CH$_2$OCH$_2$C≡CH | H | |
| 2.17 | — | F | Cl | CH$_3$ | CH$_3$ | CH$_3$ | n$_D^{27}$ 1.5252 |
| 2.18 | — | F | Cl | CH$_3$ | CH$_3$ | C$_2$H$_5$ | |
| 2.19 | — | F | Cl | CH$_3$ | CH$_3$ | C$_3$H$_7$n | |
| 2.20 | 3-CH$_3$ | F | H | CH$_3$ | CH$_3$ | CH(CH$_3$)$_2$ | |
| 2.21 | — | F | Cl | CH$_3$ | C$_2$H$_5$ | CH$_3$ | |
| 2.22 | — | F | Cl | CH$_3$ | C$_2$H$_5$ | C$_2$H$_5$ | |
| 2.23 | — | F | Cl | CH$_3$ | C$_2$H$_5$ | C$_3$H$_7$n | |
| 2.24 | 3,4-(CH$_3$)$_2$ | F | Cl | CH$_3$ | C$_2$H$_5$ | CH(CH$_3$)$_2$ | |
| 2.25 | — | F | H | CH$_3$ | H | H | m.p. 160° |
| 2.26 | — | F | H | CH$_3$ | CH$_3$ | CH$_3$ | resin |
| 2.27 | — | F | H | CH$_3$ | C$_2$H$_5$ | CH$_3$ | |
| 2.28 | — | F | H | CH$_3$ | C$_2$H$_5$ | C$_2$H$_5$ | |
| 2.29 | 3-(CH$_3$) | F | H | CH$_3$ | C$_2$H$_5$ | CH(CH$_3$)$_2$ | |
| 2.30 | — | F | H | CH$_3$ | C$_2$H$_5$ | C$_3$H$_7$n | |
| 2.31 | — | F | Cl | CH$_3$ | CH$_2$OCH$_2$C≡CH | H | |
| 2.32 | — | F | F | CH$_3$ | CH$_3$ | H | n$_D^{26}$ 1.5347 |
| 2.33 | — | F | F | CH$_3$ | CH$_3$ | CH$_3$ | resin |
| 2.34 | — | F | H | CH$_3$ | C$_2$H$_5$ | H | m.p. 65–67° |
| 2.35 | — | F | Cl | —CH$_2$Br | CH$_3$ | H | n$_D^{23}$ 1.5410 |
| 2.36 | — | F | H | CH$_3$ | CH$_3$ | H | n$_D^{26}$ 1.5347 |
| 2.37 | — | F | H | CH$_3$ | C$_3$H$_7$-n | H | n$_D^{26}$ 1.5193 |
| 2.38 | 3-CH$_3$ | F | Br | CH$_3$ | CH$_3$ | CH$_3$ | |
| 2.39 | 4-CH$_3$ | F | Br | CH$_3$ | CH$_3$ | CH$_3$ | |
| 2.40 | — | F | Br | CH$_3$ | H | H | |
| 2.41 | — | F | Br | CH$_3$ | CH$_3$ | H | |
| 2.42 | — | F | Br | CH$_3$ | C$_2$H$_5$ | H | |
| 2.43 | — | F | Br | CH$_3$ | C$_3$H$_7$ | H | |
| 2.44 | — | F | Br | CH$_3$ | CH(CH$_3$)$_2$ | H | |
| 2.45 | — | F | Br | CH$_3$ | C$_4$H$_9$(n) | H | |
| 2.46 | — | F | Br | CH$_3$ | CH$_2$Cl | H | |
| 2.47 | — | F | Br | CH$_3$ | CH$_2$OH | H | |
| 2.48 | — | F | Br | CH$_3$ | CH$_3$ | CH$_3$ | |
| 2.49 | — | F | Br | CH$_3$ | CH$_3$ | C$_2$H$_5$ | |
| 2.50 | 3-CH$_3$ | F | Cl | CH$_3$ | CH$_3$ | CH$_3$ | |
| 2.51 | 4-CH$_3$ | F | Cl | CH$_3$ | CH$_3$ | CH$_3$ | |

TABLE 2A

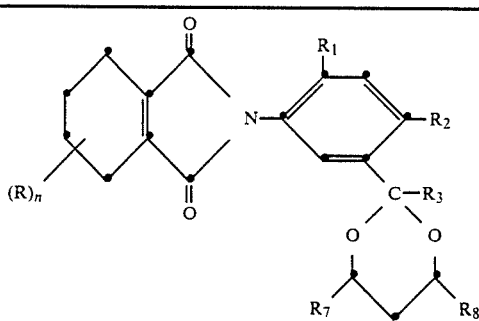

| No. | (R)$_n$ | R$_1$ | R$_2$ | R$_3$ | R$_7$ | R$_8$ | Physical data (°C.) |
|---|---|---|---|---|---|---|---|
| 2.52 | — | F | H | CH$_3$ | H | CH$_3$ | m.p. 132° |
| 2.53 | — | F | Cl | CH$_3$ | H | H | m.p. 152–153° |

TABLE 2B

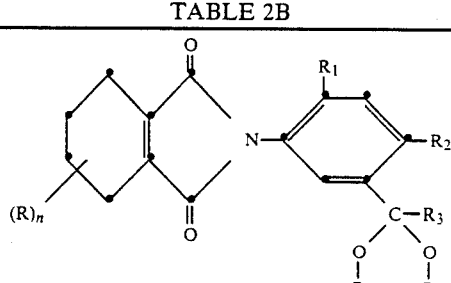

| No. | (R)$_n$ | R$_1$ | R$_2$ | R$_3$ | R$_7$ | R$_8$ |
|---|---|---|---|---|---|---|
| 2.54 | — | F | Cl | CH$_3$ | CH$_3$ | CH$_3$ |
| 2.55 | — | F | Cl | CH$_3$ | C$_2$H$_5$ | C$_2$H$_5$ |
| 2.56 | — | F | Cl | CH$_3$ | C$_3$H$_7$ | C$_3$H$_7$ |
| 2.57 | — | F | Cl | CH$_3$ | CH(CH$_3$)$_2$ | CH(CH$_3$)$_2$ |
| 2.58 | — | F | Cl | CH$_3$ | —C$_4$H$_9$-n | —C$_4$H$_9$-n |
| 2.59 | — | F | Br | CH$_3$ | —CH$_3$ | —CH$_3$ |
| 2.60 | — | F | Br | CH$_3$ | C$_2$H$_5$ | C$_2$H$_5$ |
| 2.61 | — | F | Br | CH$_3$ | C$_3$H$_7$-n | C$_3$H$_7$-n |

TABLE 2B-continued

[Structure with (R)n, R1, R2, C-R3 with OR7 and OR8]

| No. | (R)n | R1 | R2 | R3 | R7 | R8 |
|---|---|---|---|---|---|---|
| 2.62 | — | F | Br | $CH_3$ | $CH(CH_3)_2$ | $CH(CH_3)_2$ |
| 2.63 | — | F | Br | $CH_3$ | $-C_4H_9$-n | $C_4H_9$-n |
| 2.64 | 4-$CH_3$ | F | Cl | $CH_3$ | $CH_3$ | $CH_3$ |
| 2.65 | 3-$CH_3$ | F | Cl | $CH_3$ | $CH_3$ | $CH_3$ |

EXAMPLE 3

Production of 2-chloro-4-fluoro-(N-3,4,5,6-tetrahydrophthalimido)-acetophenone oxime

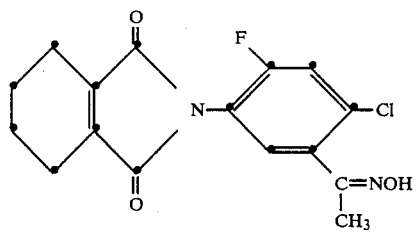

A mixture of 3.2 g of 2-chlOrO-4-fluoro-5-(N-3,4,5,6-tetrahydrophthalimido)-acetophenone, 0.8 g of hydroxylamine, hydrochloride and 50 ml of ethanol is refluxed with stirring for 2 hours. After completion of the reaction, the solution is concentrated by evaporation; the residue is then taken up in methanol, purified with active charcoal and filtered. The filtrate is again concentrated by evaporation, and 2-chloro-4-fluoro-5-(N-3,4,5,6-tetrahydrophthalimido)-acetophenone oxime crystallises out from the residue. The yield is 2.5 g, melting point 179° C.

In a manner analogous to that of this Example, there are produced the 5-(N-3,4,5,6-tetrahydrophthalic acid)acetophenone oximes listed in Tables 3 and 3A:

TABLE 3

[Structure with R1, R2, C=N-O-Q, CH3]

| No. | R1 | R2 | Q | Physical data (°C.) |
|---|---|---|---|---|
| 3.01 | F | Cl | H | m.p. 179° |
| 3.02 | F | H | H | m.p. 186° |
| 3.03 | F | F | H | m.p. 142° |
| 3.04 | Cl | Cl | H | |
| 3.05 | F | Cl | $CH_3$ | $n_D^{27}$ 1.5479 |
| 3.06 | F | Cl | $C_2H_5$ | $n_D^{22}$ 1.5469 |
| 3.07 | F | Cl | $C_3H_7$n | |
| 3.08 | F | Cl | $CH(CH_3)_2$ | |
| 3.09 | F | Cl | $CH_2CN$ | |
| 3.10 | F | Cl | $C_2H_4OCH_3$ | |
| 3.11 | F | Cl | $CH_2CH=CH_2$ | $n_D^{26}$ 1.5528 |
| 3.12 | F | Cl | $CH_2CCl=CH_2$ | |
| 3.13 | F | Cl | $CH_2CH=CHCl$ | $n_D^{26}$ 1.5158 |
| 3.14 | F | Cl | $CH_2C\equiv CH$ | |
| 3.15 | F | Cl | hexyl | $n_D^{26}$ 1.5683 |
| 3.16 | F | Cl | $CH_2COOCH_3$ | resin |
| 3.17 | F | Cl | $CH_2COOC_2H_5$ | |
| 3.18 | F | Cl | $CH_2COOCH(CH_3)_2$ | |
| 3.19 | F | Cl | $CH_2CONH_2$ | |
| 3.20 | F | Cl | $CH(CH_3)COOCH_3$ | $n_D^{30}$ 1.5215 |
| 3.21 | F | Cl | $CH(CH_3)COOC_2H_5$ | |
| 3.22 | F | Cl | $CH(CH_3)COOC_3H_7$n | |
| 3.23 | F | Cl | $CH(CH_3)COOCH(CH_3)_2$ | |
| 3.24 | F | Cl | $CH(CH_3)COOC_4H_9$n | |
| 3.25 | F | Cl | $CH(CH_3)COSCH_3$ | |
| 3.26 | F | Cl | $CH(CH_3)COOCH_2CH=CH_2$ | |
| 3.27 | F | Cl | $CH(CH_3)COOCH_2C\equiv CH$ | |
| 3.28 | F | Cl | $COCH_3$ | |
| 3.29 | F | Cl | benzoyl | |
| 3.30 | F | Cl | cyclopropanoyl | |
| 3.31 | F | Cl | $SO_2CH_3$ | |
| 3.32 | F | Cl | $SO_2N(CH_3)_2$ | |
| 3.33 | F | Cl | $COOCH_3$ | |
| 3.34 | F | Cl | $COOC_2H_5$ | |
| 3.35 | F | Cl | $COSCH_3$ | |
| 3.36 | F | Cl | $COSC_2H_5$ | |
| 3.37 | F | Cl | $CONHCH_3$ | |
| 3.38 | F | Cl | $CONH$(4-chlorophenyl) | |
| 3.39 | F | Cl | benzyl | m.p. 130–132° |
| 3.40 | F | Cl | 4-chlorobenzyl | |
| 3.41 | F | Cl | 2-chlorobenzyl | $n_D^{28}$ 1.5672 |
| 3.42 | F | Cl | 4-methylbenzyl | |
| 3.43 | F | Cl | benzoylmethyl | |
| 3.44 | F | Cl | 2-furylcarbonyl | |
| 3.45 | F | Cl | 2-thienylcarbonyl | |
| 3.46 | F | H | $CH(CH_3)COOCH_3$ | $n_D^{30}$ 1.5394 |
| 3.47 | Cl | Cl | $CH(CH_3)COOCH_3$ | $n_D^{25}$ 1.5482 |
| 3.48 | F | Cl | $C_4H_9$n | $n_D^{26}$ 1.5469 |
| 3.49 | F | Cl | $C(CH_3)_3$ | $n_D^{26}$ 1.5159 |
| 3.50 | F | F | 2-chlorobenzyl | m.p. 93–94° |
| 3.51 | F | F | benzyl | m.p. 107–109° |
| 3.52 | F | Cl | $(CH_2)_5CH_3$ | $n_D^{26}$ 1.5383 |
| 3.53 | F | F | $CH(CH_3)COOCH_3$ | $n_D^{25}$ 1.5275 |
| 3.54 | H | Cl | $CH(CH_3)COOCH_3$ | |
| 3.55 | H | Cl | $CH(CH_3)COOCH(CH_3)_2$ | |
| 3.56 | F | Cl | $CH(CH_3)COOCH_2CH(CH_3)_2$ | |
| 3.57 | F | Cl | $CH(CH_3)COOCH(CH_3)C_2H_5$ | |
| 3.58 | H | Cl | $CH_2COOCH_3$ | |
| 3.59 | Cl | Cl | $CH_2COOCH_3$ | |
| 3.60 | Cl | Cl | $CH_3$ | |
| 3.61 | F | Cl | $CH(CH_3)-CN$ | |
| 3.62 | F | Cl | 1,3-dioxolan-2-ylmethyl | |
| 3.63 | F | Br | H | |
| 3.64 | F | Br | $-CH_3$ | |
| 3.65 | F | Br | $C_2H_5$ | |
| 3.66 | F | Br | $-C_3H_7$-n | |
| 3.67 | F | Br | $CH(CH_3)_2$ | |
| 3.68 | F | Br | $-CH_2-CN$ | |
| 3.69 | F | Br | $C_2H_4OCH_3$ | |
| 3.70 | F | Br | $CH_2-CH=CH_2$ | |
| 3.71 | F | Br | $CH_2-C(Cl)=CH_2$ | |
| 3.72 | F | Br | $-CH_2-CH=CHCl$ | |
| 3.73 | F | Br | $-CH_2-C\equiv CH$ | |
| 3.74 | F | Br | cyclohexyl | |
| 3.75 | F | Br | $-CH_2-COOCH_3$ | |

TABLE 3-continued

[Structure: phthalimido-phenyl with R1, R2, and C(=N-O-Q)CH3 group]

| No. | R₁ | R₂ | Q | Physical data (°C.) |
|---|---|---|---|---|
| 3.76 | F | Br | —CH₂—COOC₂H₅ | |
| 3.77 | F | Br | —CH₂—COOCH(CH₃)₂ | |
| 3.78 | F | Br | —CH₂—CONH₂ | |
| 3.79 | F | Br | —CH(CH₃)COOCH₃ | |
| 3.80 | F | Br | —CH(CH₃)COOC₂H₅ | |
| 3.81 | F | Br | —CH(CH₃)COOC₃H₇ | |
| 3.82 | F | Br | —CH(CH₃)COOCH(CH₃)₂ | |
| 3.83 | F | Br | —CH(CH₃)COOC₄H₉(n) | |
| 3.84 | F | Br | —CH(CH₃)COOC₄H₉(s) | |
| 3.85 | F | Br | —CH(CH₃)COOC₄H₉(i) | |
| 3.86 | F | Br | —CH(CH₃)COSCH₃ | |
| 3.87 | F | Br | —CH(CH₃)COOCH₂—CH=CH₂ | |
| 3.88 | F | Br | —CH(CH₃)COOCH₂—C≡CH | |
| 3.89 | F | Br | —CO—CH₃ | |
| 3.90 | F | Br | benzyl | |
| 3.91 | F | Br | -cyclopropanoyl | |
| 3.92 | F | Br | SO₂—CH₃ | |
| 3.93 | F | Br | SO₂—N(CH₃)₂ | |
| 3.94 | F | Br | —COOCH₃ | |
| 3.95 | F | Br | —COOC₂H₅ | |
| 3.96 | F | Br | —COSCH₃ | |
| 3.97 | F | Br | —COSC₂H₅ | |
| 3.98 | F | Br | CONHCH₃ | |
| 3.99 | F | Br | CONH-(4-chlorophenyl) | |
| 3.100 | F | Br | benzyl | |

TABLE 3A

[Structure: methyl-substituted phthalimido-phenyl with R1, R2, and C(=N-O-Q)CH3 group]

| No. | R₁ | R₂ | Q | Physical data |
|---|---|---|---|---|
| 3.101 | F | Cl | H | |
| 3.102 | F | Cl | CH₃ | |
| 3.103 | F | Cl | C₂H₅ | |
| 3.104 | F | Cl | —CH₂—COOCH₃ | |
| 3.105 | F | Cl | —CH(CH₃)—COOCH₃ | |
| 3.106 | F | Cl | —CH(CH₃)—COO—C₂H₅ | |
| 3.107 | F | Cl | —CH(CH₃)COOCH(CH₃)₂ | |
| 3.108 | F | Cl | —CH(CH₃)COOC₄H₉-n | |
| 3.109 | F | Cl | —CH(CH₃)COOCH₂CH(CH₃)₂ | |
| 3.110 | F | Cl | —CH(CH₃)COOCH(CH₃)C₂H₅ | |

EXAMPLE 4

Production of methoximino-[2-chloro-4-fluoro-5-(N-3,4,5,6-tetrahydrophthalimido)-benzoyl cyanide (2-chloro-4-fluoro-5-(N-3,4,5,6-tetrahydrophthalimido)-phenylglyoxylonitril-2-oximinomethyl ether)

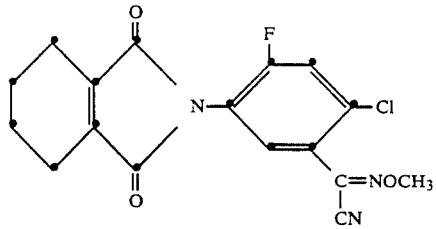

A mixture of 8.5 g of 5-amino-2-chloro-4-fluoro-phenylglyoxylonitril-2-oximino ether, 3 g of 3,4,5,6-tetrahydrophthalic anhydride and 100 ml of propionic acid is stirred for 12 hours at reflux temperature. The reaction mixture is then concentrated in vacuo; the residue is subsequently taken up in toluene/hexane and caused to crystallise. The yield is 8.5 g of the title product which melts at 97°-99° C.

The 5-amino-2-chloro-4-fluorophenylglyoxylonitril2-oximino ether required as starting product is produced as follows:

(a) Sodium salt of the oxime of 2-chloro-4-fluorobenzoylcyanide (2-chloro-4-fluorophenylglyoxylonitril-2-oxime sodium salt In a three-necked flask, 9.2 g of sodium are dissolved in 300 ml of ethanol in a nitrogen atmosphere with stirring. There are then added dropwise at room temperature firstly 67.7 g of 2-chloro-4-fluorobenzyl cyanide and then 48 g of isopentyl nitrite. There is thus formed a yellow suspension which is stirred for a further 4 hours at room temperature and subsequently concentrated by evaporation. The residue is taken up in methylene chloride and filtered. The filter residue is the desired sodium salt: yield 82 g; m.p. 287° C.

The free oxime is obtained by stirring up in dilute hydrochloric acid, m.p. 129° C.

(b) Methoximino-2-chloro-4-fluorobenzoyl cyanide (2-chloro-4-fluorophenylglyoxylonitril-2-oximinomethyl ether)

A mixture of 40 g of the sodium salt of the oxime of 2-chloro-4-fluorobenzoyl cyanide (2-chloro-4-fluoro-phenylglyoxylonitril-2-oxime), 30 g of methyl iodide and 500 ml of methyl ethyl ketone is stirred at 60° C. for 12 hours. The reaction mixture is then filtered, and the filtrate is concentrated by evaporation to thus obtain 24 g of the title product having a melting point of 66°-67° C.

(c) Methoximino-2-chloro-4-fluoro-5-nitrobenzoyl cyanide (2-chloro-4-fluoro-5-nitrophenylglyoxylonitril-2-oximinomethyl ether There are carefully added in small portions at 0° C., with stirring, 21.2 g of 2-chloro-4-fluorophenyloxylonitril-2-oximinomethyl ether in 200 ml of concentrated sulfuric acid, in the process of which a yellow solution is formed. To this are then slowly added dropwise 4.5 ml of fuming nitric acid. After the dropwise addition is completed, the solution is allowed to warm up to room temperature, and is stirred for a further 3 hours. The reaction mixture is subsequently poured onto ice; the occurring precipitate is afterwards filtered off with suction and dried. The yield is 23 g of the title product which melts at 85°–86° C.

Methoximino-5-amino-2-chloro-4-fluorobenzoyl cyanide
(5-amino-2-chloro-4-fluorophenylglyoxylonitril-2oximinomethyl ether A mixture of 12 g of 2-chloro-4-fluoro-5-nitrophenyl-glyoxylonitril-2-oximinomethyl ether, 37.2 g of tin dichloride dihydrate and 43 ml of concentrated hydrochloric acid is heated to 100 C, and is stirred at this temperature for a further 10 minutes. The reaction mixture is then poured onto ice, it is rendered alkaline with a sodium bicarbonate solution, and the organic material is extracted with ethyl acetate The organic phase is dried over sodium sulfate, filtered, and concentrated by evaporation. The residue is the desired amine: yield 9 g; m.p. 71° C.

EXAMPLE 5

Production of isopropoxycarbonyl-eth-1-yl-oximino[2-chloro-4-fluoro-5-(N-3,4,5,6-tetrahydrophthalimido)]benzoyl cyanide extracted with methylene chloride. The methylene chloride phase is dried over sodium sulfate, and concentrated by evaporation to leave 10.5 g of 2-chloro-4-fluoro-5nitrobenzyl cyanide in the form of white crystals having a melting point of 67°–68° C.

(b) 5-Amino-2-chloro-4-fluorobenzyl cyanide

Hydrogen is injected at 25°–30° C., under normal pressure, into a mixture consisting of 8.9 g of 2-chloro-4-fluoro-5-nitrobenzyl cyanide, 1 g of Raney nickel in 90 ml of absolute ethanol, until the stoichiometric amount of hydrogen has been absorbed. After completion of the absorption of hydrogen, the reaction mixture is filtered and the alkaline filtrate is concentrated by evaporation. The residue consists of 7.5 g of 5-amino-2-chloro-4-fluorobenzyl cyanide having a melting point of 85°–86° C.

(c) 5-Amino-2-chloro-4-fluorobenzoyl cyanide oxime sodium salt
(5-Amino-2-chloro-4-fluorophenylglyoxylonitril-2-oxime sodium salt)

0.3 g of sodium in 20 ml of absolute ethanol is introduced, with stirring, into a three-necked flask. There are then added slowly dropwise at room temperature, with stirring, firstly 1.8 g of 5-amino-2-chloro-4-fluorobenzyl cyanide and subsequently 1.5 ml of isopentylnitrite. The reaction solution is stirred at room temperature for a further 15 hours, and afterwards concentrated by evaporation. The residue is is taken up in glacial

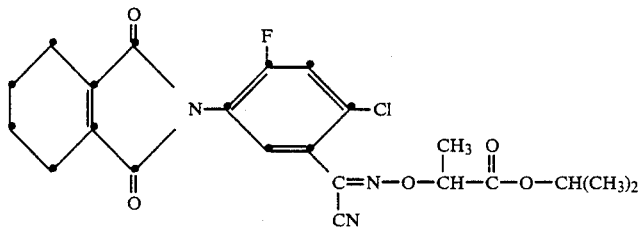

A mixture of 1.5 g of isopropoxycarbonyl-eth-1-yloximino-(5-amino-2-chloro-4-fluoro)-benzoyl cyanide, 0.7 g of 3,4,5,6-tetrahydrophthalic anhydride in 30 ml of concentrated acetic acid is stirred at the refluxing temperature for 18 hours. The reaction mixture is then poured onto ice, and the organic material which has precipitated is extracted with methylene chloride. The methylene chloride phase is dried, and concentrated by evaporation to leave 1.6 g of the title substance in the form of oil having a refractive index of $n_D^{20} = 1.5320$.

The isopropoxycarbonyl-eth-1-yl-oximino-(5-amino-2-chloro-4-fluoro)-benzoyl cyanide required as starting material is obtained as follows:

(a) 2-Chloro-4-fluoro-5-nitrobenzyl cyanide 10 g of 2-chloro-4-fluorobenzyl cyanide are dissolved at a temperature of −10° C., with stirring, in 85 ml of concentrated sulfuric acid, in the process of which a fine light-brown suspension is formed. There are then slowly added dropwise at −20° C., with stirring, 5 ml of fuming nitric acid. After completion of the addition, stirring is continued for a further half hour, the temperature rising to 0° C. The reaction mixture is poured onto 500 g of ice, and the substance which precipitates is acetic acid, stirred up and filtered to thus obtain 2.2 g of the sodium salt of 5-amino-2-chloro-4-fluorobenzoyl cyanide which melts at 263°–264° C.

The free oxime is obtained by stirring up the salt in dilute hydrochloric acid; m.p. 142°–143° C.

(d) Isopropoxycarbonyl-eth-1-yloximino-(5-amino-2-chloro-4-fluoro)-benzoyl cyanide A mixture of 1.2 g of the sodium salt of 5-amino-2-chloro-4-fluorobenzoyl cyanide, 1 ml of 2-bromopropionic acid isopropyl ester and 10 ml of acetone is stirred for 3 hours at room temperature. The solid inorganic constituents are then filtered off, and the filtrate is concentrated by evaporation to thus leave as residue 1.5 g of isopropoxycarbonyl-eth-1-yloximino-(5-amino-2-chloro-4-fluoro)benzoyl cyanide in the form of viscous oil, which can be directly further processed.

In a manner analogous to that of Examples 4 and 5, there are produced the 5-(N-3,4,5,6-tetrahydrophthalimido)benzoyl cyanide oxime ethers listed in Tables 4, 4A and 4B.

TABLE 4

[Structure: cyclohexane-1,3-dione with N-phenyl substituent bearing R₁, R₂, and C(CN)=N—O—Q group]

| No. | R₁ | R₂ | Q | Physical data (°C.) |
|---|---|---|---|---|
| 4.01 | F | Cl | H | |
| 4.02 | F | F | H | |
| 4.03 | Cl | Cl | H | |
| 4.04 | F | H | H | |
| 4.05 | F | Cl | CH₃ | m.p. 97–99° |
| 4.06 | F | Cl | C₂H₅ | m.p. 125° |
| 4.07 | F | Cl | C₃H₇n | |
| 4.08 | F | Cl | CH(CH₃)₂ | m.p. 98–99° |
| 4.09 | F | Cl | CH₂CH=CH₂ | |
| 4.10 | F | Cl | CH₂CCl=CH₂ | |
| 4.11 | F | Cl | CH₂C≡CH | |
| 4.12 | F | Cl | CH₂COOCH₃ | |
| 4.13 | F | Cl | CH₂COOC₂H₅ | |
| 4.14 | F | Cl | CH₂COOCH(CH₃)₂ | |
| 4.15 | F | Cl | CH₂COSCH₃ | |
| 4.16 | F | Cl | CH(CH₃)COOCH₃ | $n_D^{22}$ 1.5412 |
| 4.17 | F | Cl | CH(CH₃)COOC₂H₅ | |
| 4.18 | F | Cl | CH(CH₃)COOC₄H₉n | |
| 4.19 | F | Cl | CH(CH₃)COOCH₂CH=CH₂ | |
| 4.20 | F | Cl | CH(CH₃)COOCH₂C≡CH | |
| 4.21 | F | Cl | CH(CH₃)COSCH₃ | |
| 4.22 | F | Cl | COCH₃ | |
| 4.23 | F | Cl | benzoyl | |
| 4.24 | F | Cl | 4-chlorobenzoyl | |
| 4.25 | F | Cl | COOCH₃ | |
| 4.26 | F | Cl | COOC₂H₅ | |
| 4.27 | F | Cl | CONHCH₃ | |
| 4.28 | F | Cl | CON(CH₃)₂ | |
| 4.29 | F | Cl | CONH phenyl | |
| 4.30 | F | Cl | CONH 4-chlorophenyl | |
| 4.31 | F | Cl | benzyl | |
| 4.32 | F | Cl | cyclohexyl | |
| 4.33 | F | Cl | 2-chlorobenzyl | |
| 4.37 | F | Cl | 4-methylbenzyl | |
| 4.38 | F | Cl | benzoylmethyl | |
| 4.39 | F | Cl | 2-furylcarbonyl | |
| 4.40 | F | Cl | 2-thienylcarbonyl | |
| 4.41 | F | Cl | CH(CH₃)C₂H₅ | m.p. 106–107° |
| 4.42 | F | Cl | CH₂CH(CH₃)₂ | |
| 4.43 | F | Cl | C(CH₃)₃ | |
| 4.44 | F | Cl | C₅H₁₁n | |
| 4.45 | F | Cl | CH(CH₃)COOCH₂CH(CH₃)₂ | |
| 4.46 | F | Cl | CH(CH₃)COOCH(CH₃)C₂H₅ | |
| 4.47 | F | Cl | CH(CH₃)COOC(CH₃)₃ | |
| 4.48 | F | Cl | CH(C₂H₅)COOCH₃ | |
| 4.49 | F | Cl | CH(C₂H₅)COOCH(CH₃)₂ | |
| 4.50 | F | Cl | CH₂CN | |
| 4.51 | F | Cl | CH₂CH₂OH | |
| 4.52 | F | Cl | CH₂CH₂Cl | |
| 4.53 | F | Cl | (CH₂)₃OCH₃ | |
| 4.54 | F | Cl | CH₂CH₂OC₂H₅ | |
| 4.55 | F | Cl | CH(CH₃)COOH | |
| 4.56 | F | Cl | SO₂CH₃ | m.p. 177–179° |
| 4.57 | F | Cl | SO₂N(CH₃)₂ | |
| 4.58 | F | Cl | COSCH₃ | |
| 4.59 | F | Cl | C₄H₉(n) | |
| 4.60 | F | Cl | CH(CH₃)—COOC₃H₇(n) | |
| 4.61 | F | Cl | CH(CH₃)—COOCH(CH₃)₂ | $n_D^{30}$ 1.5320 |
| 4.62 | F | Cl | CH(CH₃)—COO—CH₂—CCl=CH₂ | |
| 4.63 | F | Cl | CH(CH₃)—COO—CH₂—CH=CHCl | |
| 4.64 | F | Cl | CH(CH₃)—COO—CH₂—CH=CCl—CH₃ | |
| 4.65 | F | Cl | CH(CH₃)CN | |
| 4.66 | F | Cl | CH(CH₃)—CO—NH₂ | |
| 4.67 | F | Cl | CH(CH₃)—CS—NH₂ | |
| 4.68 | F | Cl | CO—SC₂H₅ | |
| 4.69 | F | Cl | 1,3-dioxolan-2-ylmethyl | |
| 4.70 | F | Cl | —CH₂—COOH | |
| 4.71 | F | Cl | —CH₂—COOC₃H₇-n | |

TABLE 4-continued

[Chemical structure: phthalimide-N-linked phenyl group with R₁, R₂ substituents and C(CN)=N-O-Q group]

| No. | R₁ | R₂ | Q | Physical data (°C.) |
|---|---|---|---|---|
| 4.72 | F | Cl | —CH₂—COOC₄H₉-n | |
| 4.73 | F | Cl | —CH₂—COOCH₂—CH(CH₃)₂ | |
| 4.74 | F | Cl | —CH₂—COOCH(CH₃)C₂H₅ | |
| 4.75 | F | Cl | —CH₂—C(CH₃)₃ | |
| 4.76 | F | Cl | —CH₂—CH=CH₂ | |
| 4.77 | F | Cl | —CH₂—C≡CH | |
| 4.78 | F | Br | H | |
| 4.79 | F | Br | CH₃ | |
| 4.80 | F | Br | C₂H₅ | |
| 4.81 | F | Br | C₃H₇-n | |
| 4.82 | F | Br | CH(CH₃)₂ | |
| 4.83 | F | Br | C₄H₉-n | |
| 4.84 | F | Br | CH₂—CH(CH₃)₂ | |
| 4.85 | F | Br | CH(CH₃)—CH₂—CH₃ | |
| 4.86 | F | Br | C₅H₁₁-n | |
| 4.87 | F | Br | CH₂—CH=CH₂ | |
| 4.88 | F | Br | CH₂—C=CH₂ with Cl substituent | |
| 4.89 | F | Br | CH₂—CH=CHCl | |
| 4.90 | F | Br | CH₂—CH=CCl—CH₃ | |
| 4.91 | F | Br | CH₂—C≡CH | |
| 4.92 | F | Br | CH₂CH₂—OCH₃ | |
| 4.93 | F | Br | CH₂—CH₂—O—C₂H₅ | |
| 4.94 | F | Br | CH₂—COOH | |
| 4.95 | F | Br | CH₂—COOCH₃ | |
| 4.96 | F | Br | CH₂—COOC₂H₅ | |
| 4.97 | F | Br | CH₂—COOCH(CH₃)₂ | |
| 4.98 | F | Br | CH₂—COSCH₃ | |
| 4.99 | F | Br | CH(CH₃)COOH | |
| 4.100 | F | Br | CH(CH₃)COOCH₃ | |
| 4.101 | F | Br | CH(CH₃)COOC₂H₅ | |
| 4.102 | F | Br | CH(CH₃)—COOC₃H₇ | |
| 4.103 | F | Br | CH(CH₃)—COOCH(CH₃)₂ | |
| 4.104 | F | Br | CH(CH₃)—COOC₄H₉-n | |
| 4.105 | F | Br | CH(CH₃)—COOCH(CH₃)C₂H₅ | |
| 4.106 | F | Br | CH(CH₃)—COOCH₂CH(CH₃)₂ | |
| 4.107 | F | Br | CH(CH₃)—COOCH₂—CH=CH | |
| 4.108 | F | Br | CH(CH₃)—COOCH₂—C≡CH | |
| 4.109 | F | Br | CH(CH₃)—COSCH₃ | |
| 4.110 | F | Br | —COCH₃ | |
| 4.111 | F | Br | benzoyl | |
| 4.112 | F | Br | COOCH₃ | |
| 4.113 | F | Br | COOC₂H₅ | |
| 4.114 | F | Br | COSCH₃ | |
| 4.115 | F | Br | COSC₂H₅ | |
| 4.116 | F | Br | CONHCH₃ | |
| 4.117 | F | Br | benzyl | |
| 4.118 | F | Br | CH(C₂H₅)COOCH₃ | |
| 4.119 | F | Br | CH₂—CN | |
| 4.120 | F | Br | CH(CH₃)—CN | |
| 4.121 | F | Br | CH₂—CH₂OH | |
| 4.122 | F | Br | CH₂—CH₂—Cl | |
| 4.123 | F | Br | SO₂—CH₃ | |
| 4.124 | F | Br | SO₂—N(CH₃)₂ | |
| 4.125 | F | Br | 1,3-dioxolan-2-ylmethyl | |
| 4.126 | F | Cl | CH₂—C(CH₃)=CH₂ | |
| 4.127 | F | Cl | CH₂—C(CH₃)=CH₂ | |

TABLE 4A

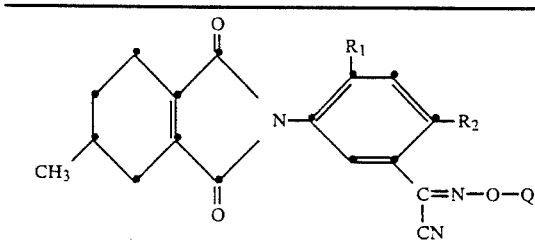

| No. | R1 | R2 | Q | Physical data |
|---|---|---|---|---|
| 4.151 | F | Br | H | |
| 4.152 | F | Br | CH3 | |
| 4.153 | F | Br | C2H5 | |
| 4.154 | F | Br | CH(CH3)2 | |
| 4.155 | F | Br | CH2—CH=CH2 | |
| 4.156 | F | Br | CH2—CH=CHCl | |
| 4.157 | F | Br | CH2—C≡CH | |
| 4.158 | F | Br | CH2—COOCH3 | |
| 4.159 | F | Br | CH(CH3)COOCH3 | |
| 4.160 | F | Br | CH(CH3)COOC2H5 | |
| 4.161 | F | Br | CH(CH3)—COO—C3H7-n | |
| 4.162 | F | Br | CH(CH3)—COOCH2—CH(CH3)2 | |
| 4.163 | F | Br | CH—(CH3)COOC4H9-n | |
| 4.164 | F | Br | CH(C2H5)COOCH3 | |
| 4.165 | F | Br | CH(CH3)COSCH3 | |

TABLE 4B

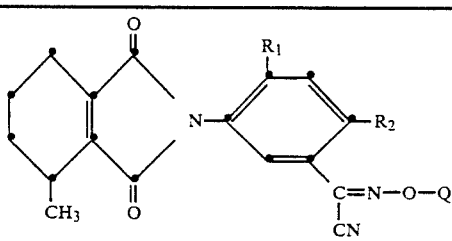

| No. | R1 | R2 | Q | Physical data |
|---|---|---|---|---|
| 4.171 | F | Cl | H | |
| 4.172 | F | Cl | CH3 | |
| 4.173 | F | Cl | C2H5 | |
| 4.174 | F | Cl | CH(CH3)2 | |
| 4.175 | F | Cl | CH2—CH=CH2 | |
| 4.176 | F | Cl | CH2—C(CH3)=CH2 | |
| 4.177 | F | Cl | CH2—CH=CHCl | |
| 4.178 | F | Cl | CH2—C≡CH | |
| 4.179 | F | Cl | CH2—COOCH3 | |
| 4.180 | F | Cl | CH—(CH3)COOCH3 | |
| 4.181 | F | Cl | CH(CH3)COOC2H5 | |
| 4.182 | F | Cl | CH(CH3)COOC3H7-n | |
| 4.183 | F | Cl | CH(CH3)COOC4H9-n | |
| 4.184 | F | Cl | CH(CH3)COOCH(CH3)C2H5 | |
| 4.185 | F | Cl | CH(CH3)COOCH2—CH(CH3)2 | |
| 4.186 | F | Cl | CH(CH3)COSCH3 | |
| 4.187 | F | Cl | CH(C2H5)COOCH3 | |

Formulation Examples

EXAMPLE 6

Formulation Examples for active ingredients of the formula I (%=per cent by weight)

| (a) Wettable powders | (a) | (b) | (c) |
|---|---|---|---|
| active ingredient according to Table 1 or 2 | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |

-continued

| (a) Wettable powders | (a) | (b) | (c) |
|---|---|---|---|
| octylphenolpolyethylene glycol ether (7–8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and the mixture ground in a suitable mill. There are thus obtained wettable powders which can be diluted with water to give suspensions of the concentration required.

| (b) Emulsion concentrates | (a) | (b) |
|---|---|---|
| active ingredient according to Table 1 or 2 | 10% | 1% |
| octylphenolpolyethylene glycol ether (4–5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentration desired can be obtained from these concentrates by dilution with water.

| (c) Dusts | (a) | (b) |
|---|---|---|
| active ingredient according to Table 1 or 2 | 0.1% | 1% |
| talcum | 99.9% | — |
| kaolin | — | 99% |

Dusts ready for use are obtained by mixing the active ingredient with the carriers, and grinding the mixture in a suitable mill.

| (d) Extruder granulates | (a) | (b) |
|---|---|---|
| active ingredient according to Table 1 or 2 | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granulate | | |
|---|---|---|
| active ingredient according to Table 1 or 2 | | 3% |
| polyethylene glycol (M.W. 200) | | 3% |
| kaolin | | 94% |

The finely ground active ingredient is uniformly applied in a mixer to the kaolin moistened with polyethylene glycol. Non-dusty coated granulates are obtained in this manner.

| (f) Suspension concentrates | (a) | (b) |
|---|---|---|
| active ingredient according to Table 1 or 2 | 40% | 5% |
| ethylene glycol | 10% | 10% |
| nonylphenolpolyethylene glycol ether (15 mols of ethylene oxide) | 6% | 1% |

-continued

| (f) Suspension concentrates | (a) | (b) |
|---|---|---|
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is obtained a suspension concentrate from which can be produced, by dilution with water, suspensions of the concentration required.

| (g) Salt solution | |
|---|---|
| active ingredient according to Table 1 or 2 | 5% |
| isopropylamine | 1% |
| octylphenolpolyethylene glycol ether (78 mols of ethylene oxide) | 3% |
| water | 91% |

Biological Examples

EXAMPLE 7

Herbicidal action before emergence of the plants

Immediately after the sowing of the test plants in trays in a greenhouse, the surface of the soil is sprayed with an aqueous dispersion of the active ingredient, the dispersion having been obtained from a 25% emulsion concentrate. Concentrations corresponding to 4 kg of active ingredient per hectare are used. The seed trays are kept in a greenhouse at 22°–25° C. with 50–70% relative humidity, and the test results are assessed after 3 weeks.

In this test, the compounds of the Tables 1 and 2 exhibit a strong herbicidal action.

EXAMPLE 8

Post-emergence herbicidal action (contact herbicide)

A number of weeds, both monocotyledonous and dicotyledonous, are sprayed after emergence (in the 4- to 6-leaf stage) with an aqueous active-ingredient dispersion at a dosage level corresponding to 4 kg of active ingredient per hectare, and the treated plants are kept at 24°–26° C. with 45–60% relative humidity. The test results are evaluated, 15 days after treatment, on the basis of the subsequently given scale of ratings In this test too, the compounds of the Tables 1 and 2 exhibit a strong to very strong herbicidal action.

EXAMPLE 9

Herbicidal action before emergence of the plants

Plastics pots are filled with expanded vermiculite (density: 0.135 g/cm$^3$, water-absorption capacity 0.565 1/1). After saturation of the non-adsorptive vermiculite with an aqueous active-ingredient emulsion in deionised water, which contains the active ingredient at a concentration of 70.8 ppm, seeds of the following plants are sown on the surface: Nasturtium officinalis, Agrostis tenuis, Stellaria media and Digitaria sanguinalis. The test vessels are subsequently kept in a climatic chamber at 20° C., with an illumination of about 20 k lux and a relative humidity of 70%. During the germination phase of 4 to days, the pots are covered over with light-permeable material in order to raise the local air humidity and watered with deionised water. After the 5th day, 0.5% of a commercial liquid fertiliser (®Greenzit) is added to the water The test is evaluated 12 days after sowing, and the effect on the test plants assessed according to the following scale of ratings:

| | |
|---|---|
| 1 | plants have died off or have not germinated, |
| 2–8 | linearly decreasing level of damage, |
| 9 | no damage: the plants have flourished as in the case of the untreated control plants. |

The results are summarised in Table 5:

TABLE 5

| Compound | Nasturtium | Stellaria | Agrostis | Digitaria |
|---|---|---|---|---|
| 1.01 | 1 | 1 | 1 | 1 |
| 1.02 | 2 | 2 | 2 | 2 |
| 1.03 | 1 | 1 | 1 | 1 |
| 1.04 | 2 | 2 | 2 | 2 |
| 1.29 | 1 | 1 | 1 | 1 |
| 1.30 | 1 | 1 | 1 | 1 |
| 2.01 | 1 | 1 | 1 | 1 |
| 2.02 | 1 | 1 | 1 | 1 |
| 2.03 | 1 | 1 | 1 | 1 |
| 2.08 | 1 | 1 | 1 | 1 |
| 2.09 | 1 | 1 | 1 | 1 |
| 2.17 | 1 | 1 | 1 | 1 |
| 2.25 | 3 | 5 | 4 | 3 |
| 2.26 | 6 | 6 | 4 | 6 |
| 2.34 | 6 | 4 | 4 | 6 |
| 2.36 | 3 | 4 | 2 | 2 |
| 2.38 | 3 | 3 | 3 | 3 |
| 2.39 | 1 | 1 | 1 | 1 |
| 2.41 | 1 | 1 | 1 | 1 |
| 3.01 | 1 | 1 | 1 | 1 |
| 3.02 | 2 | 2 | 2 | 2 |
| 3.03 | 2 | 2 | 2 | 2 |
| 3.05 | 1 | 1 | 1 | 1 |
| 3.06 | 1 | 1 | 1 | 1 |
| 3.11 | 1 | 1 | 1 | 1 |
| 3.13 | 1 | 1 | 1 | 1 |
| 3.15 | 1 | 1 | 2 | 1 |
| 3.16 | 1 | 1 | 1 | 1 |
| 3.20 | 1 | 1 | 1 | 1 |
| 3.37 | 3 | 3 | 3 | 3 |
| 3.39 | 1 | 1 | 1 | 1 |
| 3.41 | 2 | 2 | 1 | 1 |
| 3.46 | 5 | 5 | 5 | 5 |
| 3.47 | 6 | 6 | 6 | 6 |
| 3.48 | 1 | 1 | 1 | 1 |
| 3.49 | 1 | 1 | 1 | 1 |
| 3.50 | 2 | 2 | 2 | 2 |
| 3.51 | 2 | 2 | 2 | 2 |
| 3.53 | 1 | 1 | 1 | 1 |
| 4.05 | 1 | 1 | 1 | 1 |
| 4.06 | 1 | 1 | 1 | 1 |
| 4.07 | 1 | 1 | 1 | 1 |
| 4.16 | 1 | 1 | 1 | 1 |
| 4.41 | 1 | 1 | 1 | 1 |

EXAMPLE 10

Herbicidal action in the case of paddy rice

The water weeds Echinochloa crus galli and Monocharia vag. are sown in plastic containers (60 cm$^2$ surface area, 500 ml volume). After the sowing of the seeds, water is added until it is up to the level of the soil; and three days after sowing, the level of water is raised to slightly above the soil level (3–5 mm). Application of an aqueous emulsion of the test substance is made, by a spraying of the containers, three days after sowing. The applied dose corresponds to an active-substance amount of 0.5 to 4 kg per hectare (amount of spray liquor=550 liters per hectare). The plant containers are then kept in a greenhouse under optimum growth conditions for the rice weeds, that is, at 25°–30° C. with high relative humidity. The assessment of the test results is made three weeks after application of the test substance.

The compounds listed in Tables 1 and 2 attack and destroy the weeds but not the rice.

EXAMPLE 11

Reduction in growth of tropical leguminous cover crops

The test plants (*Centrosema plumieri* and *Centrosema pubescens*) are cultivated to the fully grown stage, and are then cut back to a height of 60 cm. After seven days, the active ingredient is sprayed on in the form of an aqueous emulsion. The test plants are maintained at 70% relative humidity and with 6000 lux of artificial light, 14 hours per day, at a temperature of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients from Tables 1 and 2, in an applied amount of 50–3000 g per hectare, show in this test a clear reduction in new growth (less than 20% of the new growth occurring on untreated control plants), without the test plants having suffered damage.

EXAMPLE 12

Regulation of the growth of soya beans

Soya beans of the "Hark" variety are sown in a soil/peat/sand mixture (6:3:1) in plastics containers and these are placed in a controlled-atmosphere chamber. As a result of optimum choice of temperature, illumination, supply of fertiliser and watering, the plants are able to develop during about five weeks to the 5 - 6 trifoliate leaf-stage. The plants at this point of time are sprayed with the aqueous spray liquor of an active ingredient of the formula I until they are fully wetted. The active-ingredient concentration is up to 100 g of active ingredient per hectare. An evaluation is made about five weeks after application of the spray liquor.

The active substances in Tables 1 and 2 according to the invention effect a marked increase in the number and weight of the pods in the leading shoots compared with those measured on the untreated control plants.

EXAMPLE 13

Reduction in the growth of cereals

The cereal varieties *Hordeum vulgare* (spring barley) and Secale (spring rye) are sown in plastics pots containing sterilised soil in a greenhouse, and watered as required. The young shoots are sprayed, about 21 days after sowing, with the aqueous spray liquor of an active ingredient from Tables 1 and 2. The amount of active ingredient is equivalent to up to 100 g per hectare. An assessment of the growth of the cereals is made 21 days after application.

The treated plants show a reduction of new growth (60–90% of that of control plants), and also in some cases an increase in the diameter of the stalks.

EXAMPLE 14

Reduction in the growth of grasses

The grasses *Lolium perenne, Poa pratensis, Festuca ovina, Dactylis glomerate* and *Cynodon dactylon* are sown, in a greenhouse, in plastics dishes containing a soil/peat/sand mixture (6:3:1), and watered as required. The emerged grasses are cut back weekly to a height of about 4 cm, and are sprayed, about 50 days after sowing and one day after the final cutting, with the aqueous spray liquor of an active ingredient from Tables 1 and 2. The amount of active ingredient corresponds, when converted, to up to 500 g per hectare. The growth of the grasses is assessed 21 days after application of the spray liquor.

The tested compounds of Tables 1 and 2 effect a reduction of new growth of around 10–30% compared with the new growth on the control plants.

EXAMPLE 15

Desiccation and defoliating action

Cotton plants of the Deltapine variety are grown in clay pots in a greenhouse. After the bolls have finished forming, the plants are sprayed with aqueous preparations of the active ingredient in amounts equivalent to 1.2, 0.6 and 0.3 kg per hectare in the field. Untreated plants are used as control specimens. An evaluation of the test is made 3, 7 and 14 days after application of the test substance by determining the degree of defoliation (% of leaves which have fallen) and of desiccation (% drying out of the leaves remaining on the plant).

In this test, the compounds of Table 1 in applied amounts of 0.6 and 1.2 kg/hectare, respectively, left after 7 days just a very few dried up leaves on the plants (>80% leaf-fall and desiccation).

What is claimed is:

1. A 3-aminophenoxime of the formula Va

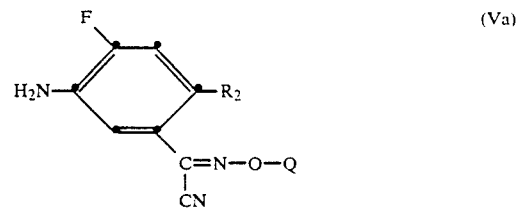

wherein
$R_2$ is chlorine or bromine,
Q hydrogen; an alkali metal ion; $C_1$–$C_{10}$-alkyl unsubstituted or mono substituted by halogen, cyano, $C_1$–$C_6$-alkoxy or $C_1$–$C_6$-alkoxycarbonyl; $C_3$–$C_8$-cycloalkyl; $C_3$–$C_8$-alkenyl unsubstituted or mono substituted by halogen; benzyl unsubstituted or mono substituted by halogen; or the 1,3-dioxolan-2-yl-methyl radical.

2. Methoximino-5-amino-2-chloro-4-fluorobenzoyl cyanide according to claim 1.

3. Sodium oximino-5-amino-2-chloro-4-fluorobenzoyl cyanide according to claim 1.

* * * * *